United States Patent
Loebl et al.

(10) Patent No.: US 11,864,947 B2
(45) Date of Patent: Jan. 9, 2024

(54) SYSTEMS AND METHODS OF OPERATION OF CAPACITIVE RADIO FREQUENCY MICRO-ELECTROMECHANICAL SWITCHES

(71) Applicant: KONINKLIJKE PHILIPS N.V., Eindhoven (NL)

(72) Inventors: Hans-Peter Loebl, Monschau-Imgenbroich (DE); Sergei Shulepov, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1234 days.

(21) Appl. No.: 16/471,997

(22) PCT Filed: Dec. 21, 2017

(86) PCT No.: PCT/EP2017/083996
§ 371 (c)(1),
(2) Date: Jun. 20, 2019

(87) PCT Pub. No.: WO2018/115226
PCT Pub. Date: Jun. 28, 2018

(65) Prior Publication Data
US 2020/0015784 A1 Jan. 16, 2020

(30) Foreign Application Priority Data
Dec. 22, 2016 (EP) .................................. 16206333

(51) Int. Cl.
*G01N 29/06* (2006.01)
*G01N 29/24* (2006.01)
*G01N 29/34* (2006.01)
*H01H 1/00* (2006.01)
(Continued)

(52) U.S. Cl.
CPC .......... *A61B 8/4494* (2013.01); *A61B 8/5207* (2013.01); *G01N 29/0654* (2013.01);
(Continued)

(58) Field of Classification Search
CPC ................ A61B 8/4494; A61B 8/5207; G01N 29/2406; G01N 29/348; G01N 29/0654;
(Continued)

(56) References Cited

U.S. PATENT DOCUMENTS 7,860,258 B2    12/2010    Azuma et al.
8,735,946 B2    5/2014    Shaheen
(Continued)

FOREIGN PATENT DOCUMENTS

EP    2246868 A1    11/2010
EP    2509125 A2    10/2012
(Continued)

OTHER PUBLICATIONS

International Search Report and Written Opinion for International Application No. PCT/EP2017/083996, filed Dec. 21, 2017, 15 pages.

*Primary Examiner* — Isam A Alsomiri
*Assistant Examiner* — Joseph C Fritchman

(57) ABSTRACT

Disclosed are systems and methods of operation for capacitive radio frequency micro-electromechanical switches, such as CMUT cells for use in an ultrasound system. An RFMEMS may include substrate, a first electrode connected to the substrate, a membrane and a second electrode connected to the membrane. In some examples, there is a dielectric stack between the first electrode and the second electrode and flexible membrane. The dielectric stack design minimizes drift in the membrane collapse voltage. In other examples, one of the electrodes is in the form of a ring, and a third electrode is provided to occupy the space in the center of the ring. Alternatively, the first and second electrodes are both in the form of a ring and there is a support between the electrodes inside the rings.

21 Claims, 12 Drawing Sheets

(51) Int. Cl.
*H01H 59/00* (2006.01)
*A61B 8/00* (2006.01)
*A61B 8/08* (2006.01)

(52) U.S. Cl.
CPC ....... *G01N 29/2406* (2013.01); *G01N 29/348* (2013.01); *H01H 1/0036* (2013.01); *H01H 59/0009* (2013.01); *H01H 2059/0018* (2013.01)

(58) Field of Classification Search
CPC ............. H01H 1/0036; H01H 59/0009; H01H 2059/0018
See application file for complete search history.

(56) References Cited

U.S. PATENT DOCUMENTS

| | | |
|---|---|---|
| 9,132,693 B2 | 9/2015 | Klootwijk et al. |
| 2006/0004289 A1 | 1/2006 | Tian et al. |
| 2008/0089181 A1* | 4/2008 | Adachi .................... A61B 8/12 367/189 |
| 2011/0163615 A1* | 7/2011 | Leonov .................... H01G 7/02 307/400 |
| 2012/0256520 A1* | 10/2012 | Torashima .......... H01L 41/0973 29/25.35 |
| 2013/0341702 A1* | 12/2013 | Kar .................... H01L 29/66833 257/324 |
| 2014/0332911 A1 | 11/2014 | Dirksen et al. |
| 2016/0213351 A1* | 7/2016 | Davidsen .............. B06B 1/0223 |
| 2017/0043343 A1* | 2/2017 | Khandros .............. C12M 23/20 |
| 2017/0136496 A1* | 5/2017 | Jacobs .................. B06B 1/0292 |
| 2018/0310916 A1* | 11/2018 | Loebl .................... B06B 1/0292 |

FOREIGN PATENT DOCUMENTS

| | | |
|---|---|---|
| WO | 2013136212 A1 | 9/2013 |
| WO | 2015044827 A1 | 4/2015 |

\* cited by examiner

SYSTEMS AND METHODS OF OPERATION OF CAPACITIVE RADIO FREQUENCY MICRO-ELECTROMECHANICAL SWITCHES

RELATED APPLICATIONS

This application is the U.S. National Phase application under 35 U.S.C. § 371 of International Application No. PCT/EP2017/083996, filed on Dec. 21, 2017, which claims the benefit of European Application No. 16206333.3, filed Dec. 22, 2016. These applications are hereby incorporated by reference herein.

FIELD OF THE INVENTION

The present invention relates to capacitive radio frequency micro-electromechanical switches, RFMEMS, and in particular to capacitive machined ultrasound transducers, CMUTs, for use in an ultrasound imaging system.

The present invention further relates to a method of operating said capacitive RFMEMS and CMUTs.

BACKGROUND OF THE INVENTION

Ultrasonic transducers used for medical imaging have numerous characteristics that lead to the production of high quality diagnostic images. Among these are broad bandwidth, enabling high resolution and high sensitivity, and large pressure output, enabling large depth of field of acoustic signals at ultrasonic frequencies. Conventionally the piezoelectric materials which possess these characteristics have been made of PZT and PVDF materials, with PZT being particularly popular as the material of choice. However, PZT suffers from a number of notable drawbacks.

Firstly, ceramic PZT materials require manufacturing processes including dicing, matching layer bonding, fillers, electroplating and interconnections that are distinctly different and complex and require extensive handling, all of which can result in transducer stack unit yields that are lower than desired. This manufacturing complexity increases the cost of the final transducer probe and puts design limitations on the minimum spacing between the elements as well as the size of the individual elements.

Moreover, PZT materials have poorly matched impedance to water or biological tissue, such that matching layers need to be added to the PZT materials in order to obtain the desired acoustic impedance matching with the medium of interest. As ultrasound system mainframes have become smaller and dominated by field programmable gate arrays (FPGAs) and software for much of the signal processing functionality, the cost of system mainframes has dropped with the size of the systems. Ultrasound systems are now available in inexpensive portable, desktop and handheld form, for instance for use as ultrasound diagnostic imaging systems or as ultrasound therapeutic systems in which a particular (tissue) anomaly is ablated using high-energy ultrasound pulses. As a result, the cost of the transducer probe is an ever-increasing percentage of the overall cost of the system, an increase which has been accelerated by the advent of higher element-count arrays used for 3D imaging in the case of ultrasound diagnostic imaging systems.

The probes used for ultrasound 3D imaging with electronic steering rely on specialized semiconductor devices application-specific integrated circuits (ASICs) which perform microbeam forming for two-dimensional (2D) arrays of transducer elements. Accordingly it is desirable to be able to manufacture transducer arrays with improved yields and at lower cost to facilitate the need for low-cost ultrasound systems, and preferably by manufacturing processes compatible with semiconductor production.

Recent developments have led to the prospect that medical ultrasound transducers can be batch manufactured by semiconductor processes. Desirably these processes should be the same ones used to produce the ASIC circuitry needed by an ultrasound probe such as a CMOS process. These developments have produced micromachined ultrasonic transducers or MUTs, the preferred form being the capacitive MUT (CMUT). CMUT transducers are tiny diaphragm-like devices with electrodes that convert the sound vibration of a received ultrasound signal into a modulated capacitance.

For transmission, the capacitive charge applied to the electrodes is modulated to vibrate/move the diaphragm of the device and thereby transmit an ultrasound wave. Since these diaphragms are manufactured by semiconductor processes the devices generally can have dimensions in the 10-500 micrometer range, with the diaphragm diameter for instance being selected to match the diaphragm diameter to the desired resonance frequency (range) of the diaphragm, with spacing between the individual diaphragms less than a few micrometers. Many such individual CMUT cells can be connected together and operated in unison as a single transducer element. For example, four to sixteen CMUT cells can be coupled together to function in unison as a single transducer element. A typical 2D transducer array can have 2000-10000 CMUT transducer elements or cells by way of example.

The manufacture of CMUT transducer-based ultrasound systems is therefore more cost-effective compared to PZT-based systems. Moreover, due to the materials used in such semiconductor processes, the CMUT transducers exhibit much improved acoustic impedance matching to water and biological tissue, which obviates the need for (multiple) matching layers and yields an improved effective bandwidth.

In order to optimize the acoustic power (output pressure) produced by the CMUT cells, the CMUT cells may be operated in so-called collapse mode in which the CMUT cells are driven by a bias voltage that drives a central part of the diaphragm or flexible membrane across the gap onto the opposing substrate and provided with a stimulus having a set frequency that causes the diaphragm or flexible membrane to resonate at the set frequency. The voltage at which the membrane goes into collapse is called the collapse voltage, $V_C$. However, a drawback of operating CMUT cells in a collapse mode is that it negatively affects the lifetime of the CMUT cells. This is largely caused by charging effects, namely polarization, charge injection and space charge orientation, which occur in the dielectric layers that separate the electrodes in the CMUT cells in the presence of the high electric field caused by the collapse voltage. A further effect of this is the shifting of the collapse voltage $V_C$, over time. CMUT cells have operational ranges of bias voltage and cell capacitance that define an operational window for the cell. A shift in bias voltage or cell capacitance lead to a shift in the transmission and reception characteristics of the CMUT cells, resulting in a negative impact on the ultrasound image quality.

A CMUT cell essentially functions as a capacitive RFMEMS switch. The issues described above, relating to drift to the CMUT cell characteristics, apply more generally to MEMS switches in particular capacitive RFMEMS switches which are based on a resonant mode of operation.

SUMMARY OF THE INVENTION

The invention is defined by the claims.

According to examples in accordance with an aspect of the invention, there is provided a capacitive radio frequency micro-electromechanical switch, RFMEMS, comprising:
a substrate;
a first electrode connected to the substrate;
a flexible membrane, wherein the flexible membrane is spatially separated from the first electrode;
a second electrode connected to the flexible membrane; and
a dielectric stack between the first electrode and the second electrode and flexible membrane, comprising:
a first dielectric layer, wherein the first dielectric layer has a first density of electrically active defects; and
a second dielectric layer, wherein the second dielectric layer has a second density of electrically active defects, lower than the first.

For example, when a capacitive RFMEMS switch has a bias voltage applied to the first electrode, an electric field will be generated between the first and second electrodes. If the bias voltage exceeds a collapse voltage of the capacitive RFMEMS switch, the switch will operate in a collapse mode, such as is used for a CMUT cell within an ultrasound system. The electric field density will be strongest within the collapsed portion of the switch as the two electrodes are closest at this point. The electric field leads to the charging of the first and second dielectric layers of the dielectric stack. The electric field causes the dielectric layers to become polarized leading to a negative shift in the collapse voltage of the switch. The degree of polarization depends of the electrically active defect density of the dielectric layer. The shift in the collapse voltage is known as a drift voltage. Thus, a drift voltage, and measurement of a drift voltage refers to a change in the collapse voltage.

A further effect of the electric field is the orientation of space charges within the dielectric layers. Charge carriers within the dielectric layers, i.e. those within the conduction band of the dielectric layers, will orientate towards the electrodes of the switch generating a space charge across the dielectric layers. The orientation of the space charges leads to a positive drift voltage. This effect dominates in dielectrics with a low electrically active defect density.

In addition, charge injection occurs in both dielectric layers due to the tunneling of charge carriers from the first and second electrodes. Charge injection results in a negative drift voltage, thereby adding to the effect of the polarization of the dielectric layers.

By providing a first and second dielectric layer that generate a negative and positive shift in collapse voltage respectively, it is possible for the two drift voltages to cancel each other out. Put another way, the overall drift voltage is minimized by the opposing charging effects of the first and second dielectric layers.

By 'between the first electrode and the second electrode and flexible membrane' is meant between the first electrode and the combination of the second electrode and the flexible membrane, or in other words, between the first electrode and both the second electrode and flexible membrane.

The dielectric stack may be connected to the first electrode (i.e. the substrate electrode), so that dielectric stack is spatially separated from the flexible membrane.

In an embodiment, the first and second dielectric layers are constructed from the same material. By preparing the two layers in a different manner, it is possible for the same material to exhibit different dielectric properties.

In an embodiment, the first and second dielectric layers comprise silicon dioxide, SiO2.

Silicon dioxide, SiO2, is a commercially available dielectric material. The dielectric properties of silicon dioxide vary depending on the method of preparation.

In some embodiments, the first dielectric layer is constructed using atomic layer deposition, ALD, leading to a greater susceptibility to polarization effects under an electric field.

By manufacturing the first dielectric layer through the atomic layer deposition of SiO2, the first dielectric layer will show a higher degree of polarization effects compared to the second layer, leading to the generation of a negative voltage drift.

In an arrangement, the second dielectric layer is constructed using chemical vapor deposition, CVD, leading to a greater susceptibility space charge orientation.

By manufacturing the second dielectric layer through the chemical vapor deposition of SiO2, the second dielectric layer will show a higher level of space charge orientation compared to the first dielectric layer, resulting in the generation of a positive voltage drift.

In some arrangements, the second dielectric layer is thicker than the first dielectric layer, for example at least two times thicker for example three times thicker.

When the first and second dielectric layers are manufactured through the ALD and CVD of SiO2 respectively, the negative voltage drift associated with the first dielectric layer can be considerably larger than the positive voltage drift associated with the second dielectric layer. By providing a thicker second dielectric layer, it is possible to compensate for this and further minimize the drift voltage.

In some embodiments, the first and second dielectric layers comprise aluminum dioxide, Al3O2, or hafnium(IV) oxide, HfO2. Al3O2 and HfO2 are further examples of commercially available dielectrics that may be prepared in first and second layers that exhibit differing dielectric properties.

In some designs, the dielectric stack further comprises:
a third dielectric layer, wherein the third dielectric layer is selected based on the dielectric properties of the first and second dielectric layers.

By providing a third dielectric layer based on the dielectric properties of the first and second dielectric layers, the minimization of the voltage drift may be further optimized. This becomes more relevant when the spatial requirements of the switch limit the changes in thickness that can be made to the first and second dielectric layers.

In a yet further design, wherein the first and second dielectric layers comprise SiO2, the third dielectric layer comprises aluminum oxide, Al2O3. In this way, the third dielectric layer does not need to be constructed from the same material as the first and second dielectric layers, meaning that the shift in the collapse voltage, i.e. the drift voltage, can be minimized through an optimal combination of dielectric properties.

In various embodiments, the capacitive RFMEMS is a capacitive micro-machined ultrasound transducer, CMUT, cell.

A capacitive micro-machined ultrasound transducer cell is an example of a capacitive RFMEMS that can be used in the ultrasonic probe of an ultrasound system for generating ultrasonic radio frequency pulses.

According to examples in accordance with an aspect of the invention, there is provided an ultrasound system comprising:
an ultrasonic probe, wherein the ultrasonic probe comprises:
an array of CMUT cells as discussed above;
a voltage supply coupled to the ultrasonic probe, wherein the voltage supply is adapted to:
provide a bias voltage between the first electrode of a CMUT cell and second electrode of a CMUT cell, wherein the bias voltage is adapted to drive the CMUT cell into a collapse mode; and
provide a stimulus voltage between the first electrode and the second electrode of the CMUT cell.

By providing an ultrasonic probe with CMUT cells comprising dielectric layers capable of minimizing the voltage drift associated with driving the cells in collapse mode, as required by an ultrasound system, the lifetime of the system and the image quality produced by the system are improved.

By operating the CMUT cells in collapse mode, the pressure output, bandwidth and operation stability of the CMUT array are able to meet the standards required for medical ultrasound imaging. Operating the CMUT cells in collapsed mode often leads to a shift in the collapse voltage of the cell, known as a drift voltage, which negatively affects the lifetime of and image quality produced by the ultrasound system; however, this is overcome by providing CMUT cells with dielectric layers capable of minimizing said drift voltage.

In some designs, the stimulus voltage is adapted to vibrate the flexible membrane of the CMUT cell at a predetermined frequency.

In this way, it is possible to generate a radio frequency (RF) pulse. For an ultrasound system, this pulse can range from 20 kHz to several tens of MHz. In various arrangements, the second electrode is adapted to detect incoming vibrations.

After an RF pulse is emitted into a subject, for example a patient, the RF pulse will travel through the subject until it meets a barrier. At a barrier, the ultrasonic waves of the RF pulse will be partially reflected back towards the ultrasound system. The ultrasonic wave will then impact the surface of the ultrasonic probe, housing the CMUT array, and cause the flexible membrane of a CMUT cell to vibrate.

In an arrangement, the system further comprises:
a signal processor, wherein the signal processor is adapted to generate data based on the incoming vibrations detected by the second electrode.

The vibrations of the flexible membrane of a CMUT cell can be detected by the second electrode. In other words, the vibration of the flexible membrane will generate an electrical signal in the second electrode. This electrical signal can then be interpreted by a signal processor and used to generate data for the construction of an ultrasound image.

According to examples in accordance with an aspect of the invention, there is provided a method for operating a capacitive RFMEMS, the capacitive RFMEMS comprising:
a substrate;
a first electrode connected to the substrate;
a flexible membrane, wherein the flexible membrane is spatially separated from the first electrode;
a second electrode connected to the flexible membrane; and
a dielectric stack between the first electrode and the second electrode and flexible membrane, comprising:
a first dielectric layer, wherein the first dielectric layer has a first density of electrically active defects; and
a second dielectric layer, wherein the second dielectric layer has a second density of electrically active defects, lower than the first,
the method comprising:
providing a bias voltage to the first electrode of the capacitive RFMEMS, thereby creating an electric field between the first and second electrode, wherein the bias voltage is adapted to drive the capacitive RFMEMS into a collapse mode;
providing a stimulus voltage to the second electrode, thereby increasing an electric field between the first and second electrode;
polarizing the first dielectric layer to a first degree of polarization and the second dielectric layer to a second degree of polarization, lower than the first degree, thereby causing a negative drift in the bias voltage between the first and second electrodes; and
orienting space charges within the first dielectric layer to a first level of orientation and within the second dielectric layer to a second level of orientation, greater than the first level, thereby causing a positive drift in the bias voltage between the first and second electrodes, thereby minimizing the overall drift in bias voltage between the first and second electrodes.

According to examples in accordance with a further aspect of the invention, there is provided a capacitive micro-machined ultrasonic transducer, CMUT, cell, the CMUT cell comprising:
a substrate;
a first electrode connected to the substrate formed around a central axis;
a flexible membrane, wherein the flexible membrane is spatially separated from the first electrode; and
a second electrode connected to the flexible membrane, wherein the second electrode is concentric with the first electrode,
wherein one of the first and second electrodes comprises a ring, and there is a third electrode which occupies a middle portion of the ring such that the ring and third electrodes are spatially separated.

When operated in collapsed mode, the collapsed region of the CMUT cell experiences the largest electric field strength. The electric field density is determined by dividing the voltage applied across the device by the thickness of the layers between the electrodes. These layers can comprise the flexible membrane and part of the substrate and may further include one or more dielectric layers. The electric field will concentrate in the layer having the lowest dielectric permittivity. This means that, whilst the electric field may not be high enough to cause a negative effect on all of the layers, the concentration of the electric field in the collapsed portion of the CMUT cell may be high enough to cause charging to occur in the layer with the lowest dielectric permittivity.

By providing one of the electrodes in the shape of a ring, thereby removing the second electrode from the collapsed portion of the CMUT cell, the electric field within the collapsed portion of cell is reduced. In this way, it is possible to reduce the charging effects caused by the electric field required to operate the CMUT in collapsed mode.

In an embodiment, the CMUT cell further comprises a third electrode connected to the flexible membrane, wherein the third electrode occupies a middle portion of the ring defined by the second electrode, such that the second and third electrodes are spatially separated.

In this way, the third electrode can be connected to the flexible membrane, so as to occupy the collapsed portion of the CMUT cell. This enables a greater control of the electric field within the collapsed portion, which may then lead to further reducing the charging effects in the collapsed portion of the cell.

In some embodiments, the third electrode is electrically grounded.

By grounding the third electrode, the collapsed portion of the CMUT cell only experiences an electric field density corresponding to the bias voltage needed to drive the cell into collapse mode. In other words, the stimulus voltage required to generate an ultrasonic RF pulse no longer contributes to the electric field density in the collapsed portion. In this way, the charging of the collapsed portion, and therefore the drift voltage, is minimized or even prevented entirely.

In various embodiments, the first electrode is connected to the flexible membrane and the second and third electrodes are connected to the substrate.

It is possible to achieve the same effects as described above in this alternate arrangement.

In some designs, the CMUT cell further comprises a support, formed about the central axis, connected between the substrate and the flexible membrane, wherein the first electrode is in the shape of a ring.

By providing a support in the central region of the CMUT cell, it is possible to operate the cell in a pre-stressed mode, which offers similar benefits to operating the cell in collapse mode. In addition, by forming the first electrode into the shape of a ring, similar to the second electrode, the electric field density in the central region, containing the support, is limited, thereby reducing charging within the CMUT cell.

According to examples in accordance with a further aspect of the invention, there is provided an ultrasound system comprising:
  an ultrasonic probe, wherein the ultrasonic probe comprises an array of CMUT cells each as discussed above;
  a voltage supply coupled to the ultrasonic probe, wherein the voltage supply is adapted to:
    provide a bias voltage between the first electrode of a CMUT cell and second electrode of a CMUT cell; and
    provide a stimulus voltage between the first electrode and the second electrode of the CMUT cell; and
  a capacitance sensing circuit.

By providing an ultrasonic probe with an array of CMUT cells, each adapted to reduce or eliminate charging effects within themselves, the lifetime of the ultrasound system and the image quality produced by the system are increased.

The charging of a CMUT cell produces a shift in the collapse voltage, known as drift voltage, between the electrodes of the cell, leading to a change in the cell's capacitance. This leads to a change in the transducer properties of the cell when operated at a constant voltage, as the transducer operation depends on both the driving voltage and the cell's capacitance. By providing the ultrasound system with a capacitance sensing circuit, it is possible to monitor the capacitance, and so the charging effects, of each CMUT cell in the CMUT array. This enables the system to monitor the condition of each cell and provide an indication to the system of when the charging of a cell may adversely affect the system's performance.

In an embodiment, the capacitance sensing circuit is adapted to:
  generate a test signal, wherein the test signal has a predetermined voltage;
  measure an attenuated signal of the test signal, wherein the test signal is attenuated by the impedance of at least the CMUT cell;
  determine an impedance of the CMUT cell based on the attenuated signal and the test signal; and
  determine a drift voltage of the CMUT cell based on the determined impedance.

As the test signal travels through the system, it is attenuated by the impedance of various components of the system such as: a low-noise amplifier; a coaxial cable connecting the ultrasonic probe to the ultrasound system; and a CMUT cell.

Using the known test signal and the measured attenuated signal, it is possible to calculate the impedance of the circuit. As the impedance of the components such as the low-noise amplifier and the coaxial cable are known, it is possible to extract the impedance of the CMUT cell.

The impedance of the CMUT cell depends on the capacitance of the cell, and so is dependent on the charging of the cell. In this way, the capacitance sensing circuit enables the ultrasound system to monitor the drift voltage, and so the level of charging, of a CMUT cell.

In an arrangement, responsive to the absolute value of the drift voltage being above a predetermined value, the voltage supply is further adapted to reverse the polarity of the bias voltage.

By reversing the polarity of the bias voltage, the charge held by the CMUT cell will be dissipated. By performing this function regularly, the CMUT cell will be prevented from building an excessive amount of charge that would lead to a negative impact of the ultrasound image quality and lifetime of the ultrasonic system.

In further or other arrangements, responsive to the absolute value of the drift voltage being above a predetermined value, the voltage supply is further adapted to reverse the polarity of the stimulus voltage.

In this way it is possible to further dissipate the charge in the CMUT cell whilst also enabling the cell to transmit the ultrasonic waves to the subject.

In some cases, the voltage supply is adapted to reverse the polarity in less than 1 microsecond.

Performing the voltage reversal in this timeframe prevents acoustic artifacts in the final ultrasound image.

According to examples in accordance with a further aspect of the invention, there is provided a method for operating a CMUT cell, the CMUT cell comprising:
  a substrate;
  a first electrode connected to the substrate;
  a flexible membrane, wherein the flexible membrane is spatially separated from the single electrode; and
  a second electrode connected to the flexible membrane;
  the method comprising performing a sequence of ultrasound generation cycles, each cycle comprising:
    providing a bias voltage to the first electrode of a CMUT cell, wherein the bias voltage drives the CMUT cell into collapsed mode;
    providing a stimulus voltage to the second electrode of the CMUT cell, wherein the stimulus voltage causes a portion of the flexible membrane to vibrate at a predetermined frequency; and
  removing the stimulus voltage, thereby enabling the CMUT cell to receive incoming acoustic signals,
  wherein the sequence comprises:
    first cycles with a first polarity of the bias voltage and second cycles with an opposite second polarity of the bias voltage, or
    third cycles with a first polarity of the stimulus voltage and fourth cycles with an opposite second polarity of the stimulus voltage.

A typical ultrasound transmission sequence will consist of a transmission setup step, a transmit step and a receive step. By using opposite polarity cycles, drift of the collapse voltage is corrected so that a more stable performance of the CMUT cell is obtained over time.

The sequence may comprise alternate first and second cycles (i.e. an alternating polarity bias voltage) or alternate third and fourth cycles (i.e. an alternating polarity stimulus voltage).

The alternating cycles may thus be implemented automatically. Instead, there may be feedback control. For example, each ultrasound generation cycle may comprises determining a drift voltage of the CMUT cell.

By determining a drift voltage of the CMUT cell in the transmission setup step, it is possible to provide a bias voltage that will prevent or counteract the charging of the CMUT cell before the transmit step begins. In this way, the CMUT cell may be discharged during the normal operation of the ultrasound system, meaning that there is no requirement for a separate discharging step.

The bias voltage selected based on the determined voltage may vary in magnitude and polarity during the transmission setup step.

The stimulus voltage is provided in order to cause the flexible membrane of the CMUT cell to vibrate at a predetermined frequency. In this way, an ultrasonic RF pulse is generated and sent into the subject, for example a patient.

Following this, the stimulus voltage is removed, enabling to the flexible membrane to vibrate freely in response to the reflected ultrasound waves returning from the subject.

In an embodiment, the step of determining a drift voltage of the CMUT cell comprises:
  generating a test signal, wherein the test signal has a predetermined voltage;
  measuring an attenuated signal of the test signal, wherein the test signal is attenuated by the impedance of at least the CMUT cell;
  determining an impedance of the CMUT cell based on the attenuated signal and the test signal; and
  determining a drift voltage of the CMUT cell based on the determined impedance.

In some embodiments, the method further comprises, responsive to determining that the absolute value of the drift voltage is above a predetermined value, reversing the polarity of the bias voltage.

In further or other embodiments, the method further comprises, responsive to determining that the absolute value of the drift voltage is above a predetermined value, reversing the polarity of the stimulus voltage.

It is noted that the methods and apparatus features may be used alone or in combination. Thus, the dielectric stack design may be used with or without the concentric electrode layout. Similarly, the method of determining the drift voltage may be applied to a design with or without the dielectric stack design, and with or without the concentric electrode design.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
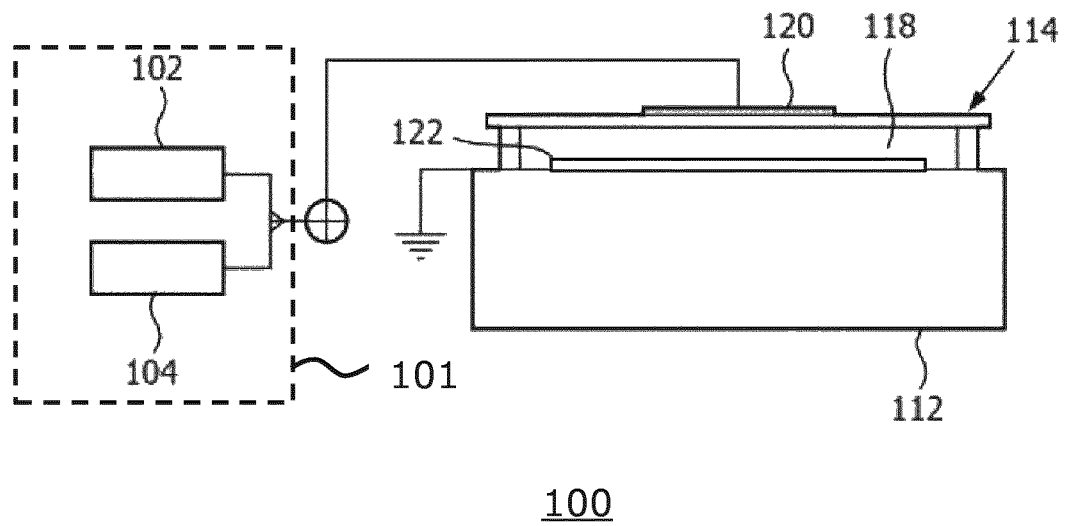
FIG. 1 schematically depicts a typical CMUT cell of an ultrasound system operable in a collapsed mode.

It should be understood that the figures are merely schematic and are not drawn to scale. It should also be understood that the same reference numerals are used throughout the figures to indicate the same or similar parts.

The invention provides systems and methods of operation for capacitive radio frequency micro-electromechanical switches, such as CMUT cells for use in an ultrasound system. An RFMEMS includes substrate, a first electrode connected to the substrate, a membrane and a second electrode connected to the membrane.

In some examples, there is a dielectric stack between the first electrode and the second electrode and flexible membrane. The dielectric stack design minimizes drift in the membrane collapse voltage. In other examples, one of the electrodes is in the form of a ring, and a third electrode is provided to occupy the space in the center of the ring. Alternatively, the first and second electrodes are both in the form of a ring and there is a support between the electrodes inside the rings.

FIG. 1 shows an aspect of an ultrasound system according to embodiments of the present invention, in which the system includes an ultrasound probe having a transducer array comprising CMUT cells 100. The CMUT cells 100 according to embodiments of the invention will be explained in more detail with the aid of FIGS. 6, 7 and 9-12. As will be explained in further detail below, such an ultrasound system may be an ultrasound diagnostic imaging system or may be an ultrasound therapeutic system.

Such a CMUT cell 100 typically comprises a flexible membrane or diaphragm 114 suspended above a silicon substrate 112 with a gap or cavity 118 there between. A first electrode 122 is located on the floor of the cell on the upper surface of the substrate 112 in this example. A second electrode 120 is located on the diaphragm 114 and moves with the diaphragm. In the example shown, the two electrodes are circular.

A dielectric (not shown) is provided on the substrate 112 and underneath the top (second) electrode 120. These two dielectrics may be equal in composition and thickness, but may be also asymmetric (different materials and thicknesses).

Other realizations of the electrode 120 design can be considered, such as electrode 120 may be embedded in the membrane 114 or it may be deposited on the membrane 114 as an additional layer. In this example, the first electrode 122 is circularly configured and embedded in the substrate layer 112 by way of non-limiting example. Other suitable arrangements, e.g. other electrode shapes and other locations of the first electrode 122, e.g. on the substrate layer 112 such that the first electrode 122 is directly exposed to the gap 118 or separated from the gap 118 by an electrically insulating layer or film to prevent a short-circuit between the second electrode 120 and the first electrode 122. In addition, the membrane layer 114 is fixed relative to the top face of the substrate layer 112 and configured and dimensioned so as to define a spherical or cylindrical cavity 118 between the membrane layer 114 and the substrate layer 112. It is noted for the avoidance of doubt that in FIG. 1 the first electrode 122 is grounded by way of non-limiting example. Other arrangements, e.g. a grounded second electrode 120 or both second electrode 120 and first electrode 122 floating are of course equally feasible.

The cell 100 and its gap 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 100 shall be understood as the biggest lateral dimension of the cell.

In FIG. 1, the diameter of the cylindrical cavity 118 is larger than the diameter of the circularly configured electrode plate 122. Electrode 120 may have the same outer diameter as the circularly configured electrode plate 122, although such conformance is not required and FIG. 1 shows a larger electrode plate 122. Thus, the second electrode 120 may be fixed relative to the top face of the membrane layer 114 so as to align with the first electrode plate 122 below. The electrodes of the CMUT cell 100 provide the capacitive plates of the device and the gap 118 is the dielectric between the plates of the capacitor. When the diaphragm vibrates, the changing dimension of the dielectric gap between the plates provides a changing capacitance which is sensed as the response of the CMUT cell 100 to a received acoustic echo.

The spacing between the electrodes is controlled by applying a static voltage, e.g. a DC bias voltage, to the electrodes with a voltage supply 101. The voltage supply 101 may optionally comprise separate stages 102, 104 for providing the DC and AC or stimulus components respectively of the drive voltage of the CMUT cells 100, e.g. in transmission mode. The first stage 102 may be adapted to generate the static (DC) voltage component and the second stage 104 may be adapted to generate an alternating variable voltage component or stimulus having a set alternating frequency, which signal typically is the difference between the overall drive voltage and the aforementioned static component thereof. The static or bias component of the applied drive voltage preferably meets or exceeds the threshold value for forcing the CMUT cells 100 into their collapsed states. This has the advantage that the first stage 102 may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component. Other suitable embodiments of the voltage source supply 101 should be apparent, such as for instance an embodiment in which the voltage source supply 101 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the voltage source supply 101 may be implemented in any suitable manner.

It is known that by applying a static voltage above a certain threshold, the CMUT cell 100 is forced into a collapsed state in which the membrane 114 collapses onto the substrate 112. This threshold value may depend on the exact design of the CMUT cell 100 and is defined as the DC bias voltage, known as the collapse voltage, at which the membrane 114 sticks to (contacts) the cell floor through the force due to the electric field between the electrodes. The amount (area) of contact between the membrane 114 and the substrate 112 is dependent on the applied bias voltage. Increasing the contact area between the membrane 114 and the substrate 112 increases the resonant frequency of the membrane 114, as will be explained in more detail with the aid of FIG. 2a and FIG. 3a.

The frequency response of a collapsed mode CMUT cell 100 may be varied by adjusting the DC bias voltage applied to the CMUT electrodes after collapse. As a result, the resonant frequency of the CMUT cell increases as a higher DC bias voltage is applied to the electrodes.

Figure 2A:
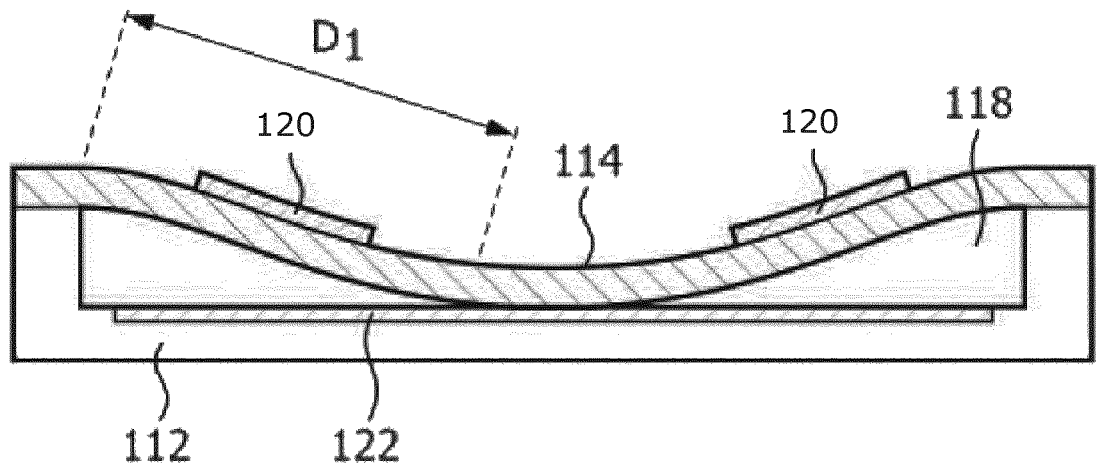
FIGS. 2a, 2b, 3a and 3b depict operating principles of such a CMUT cell.
Figure 2B:
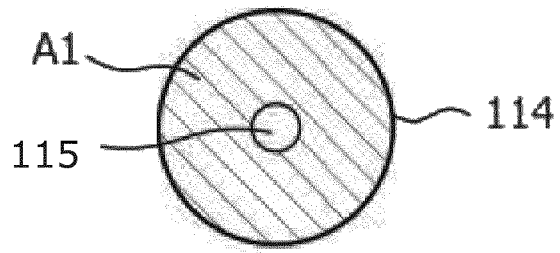
Figure 3A:
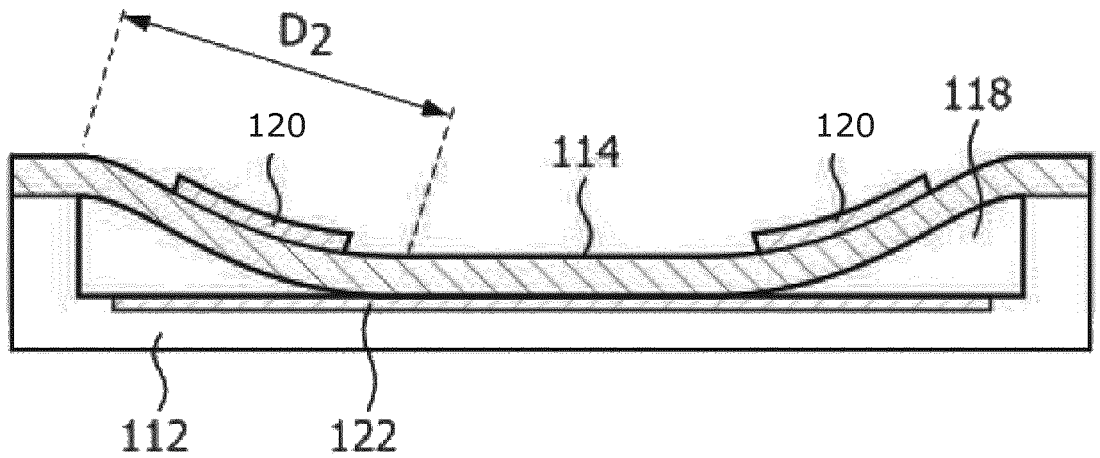

The principles behind this phenomenon are illustrated in FIGS. 2a, 2b, 3a and 3b. The cross-sectional views of FIGS. 2a and 3a illustrate this one-dimensionally by the distances D1 and D2 between the outer support of the membrane 114 and the point where the membrane begins to touch the floor of the cavity 118 in each illustration. It can be seen that the distance D1 is a relatively long distance in FIG. 2a when a relatively low bias voltage is applied, whereas the distance D2 in FIG. 3a is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 2a will be lower than the resonant frequency of the CMUT cell in FIG. 3a which is subject to the higher bias voltage.

Figure 3B:
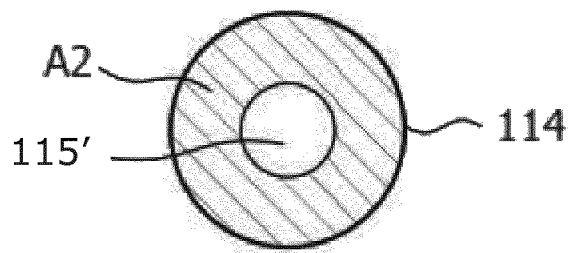

The phenomenon can also be appreciated from the two-dimensional illustrations of FIGS. 2b and 3b, which vary as a function of the effective operating area of the CMUT membrane. When the membrane 114 just touches the floor of the CMUT cell as shown in FIG. 2a, the effective vibrating area A1 of the non-contacting (free vibrating) portion of the cell membrane 114 is large as shown in FIG. 2b. The small area 115 in the center represents the center contact region of the membrane. The large area membrane will vibrate at a relatively low frequency. This area 115 is an area of the membrane 114, which is collapsed to the floor of the CMUT cell. When the membrane is pulled into deeper collapse by a higher bias voltage as in FIG. 3a, the larger central contact area 115' results in a smaller free vibrating area A2 as shown in FIG. 3b. This lesser area A2 will vibrate at a higher frequency than the larger A1 area. Thus, as the DC bias voltage is decreased the frequency response of the collapsed CMUT cell decreases, and when the DC bias voltage increases the frequency response of the collapsed CMUT cell increases.

Figure 4:
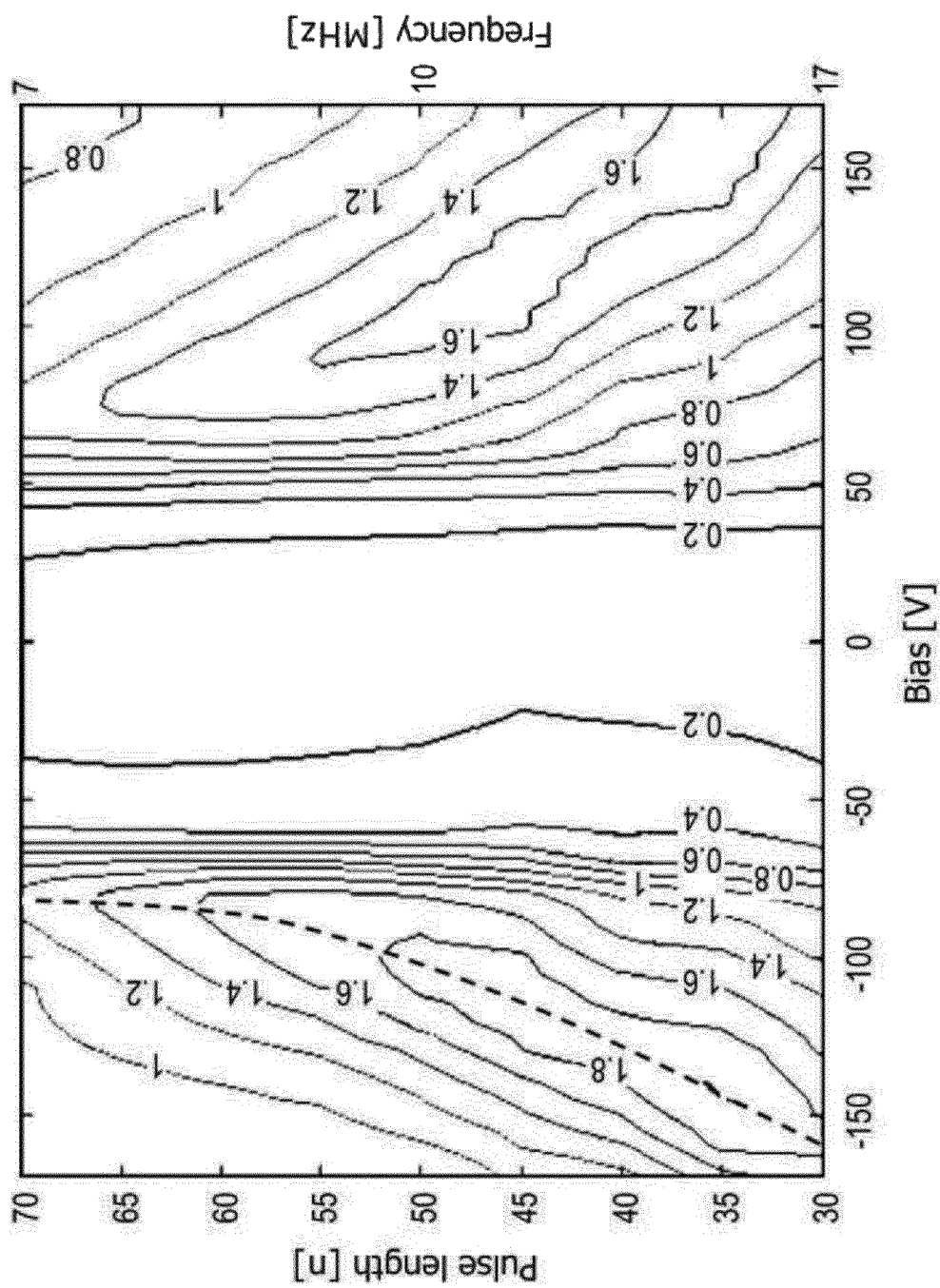
FIG. 4 is a contour plot of the acoustic performance of such a CMUT cell.

FIG. 4 shows a contour plot of the acoustic pressure output of a typical CMUT cell 100 in collapse mode as a function of applied DC bias voltage including a stimulus in the form of an AC modulation or frequency modulation of constant frequency during transmission. The reciprocal of the corresponding pulse length is double the applied frequency. As can be seen from this contour plot, when the CMUT cell 100 is operated at a fixed or static voltage, e.g. a DC bias voltage of static value, optimal acoustic performance is obtained for a small range of frequencies only. However, when varying the bias voltage and the frequency modulation on the bias voltage signal in a correlated manner, as indicated by the dashed line in the contour plot, the optimal acoustic performance of the CMUT cell 100 may be achieved over a much larger frequency range, thereby increasing the effective bandwidth of the ultrasound pulse (or pulse train) generated in the transmission mode of the ultrasound probe including the CMUT cell 100.

This can be understood in back reference to FIGS. 2a and 3a, which explained that the resonance frequency of the CMUT cell 100 in a collapsed state is a function of the applied (DC) bias voltage. By adjusting the applied bias voltage when generating ultrasonic pulses of a particular set frequency by applying a stimulus having the appropriate set frequency, pulses of different frequencies can be generated exhibiting (near-) optimal acoustic performance of the CMUT cell 100 for each pulse frequency. This therefore ensures (near-) optimal imaging resolution over a large bandwidth of the imaging spectrum.

Figure 5A:
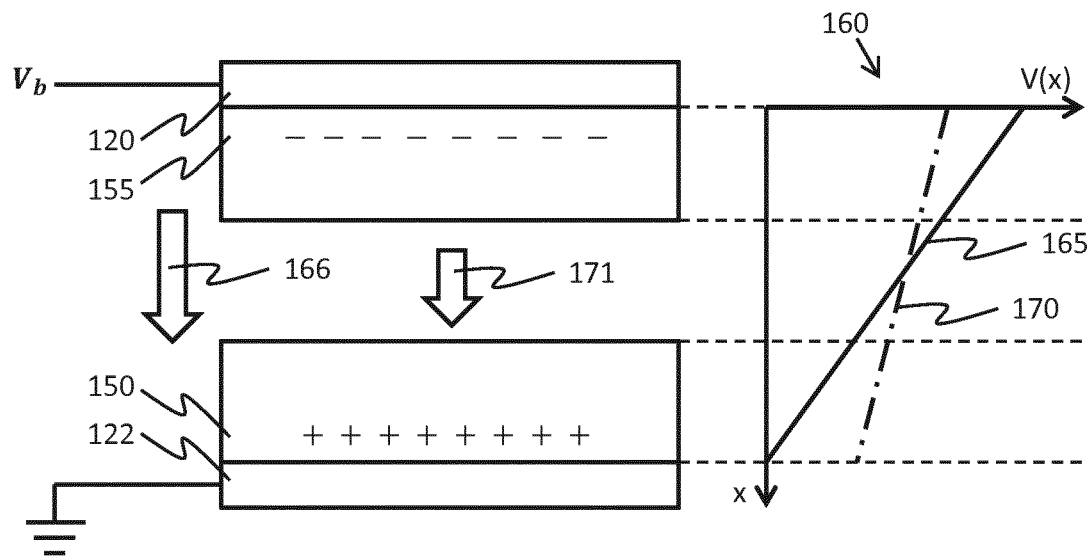
FIGS. 5a and 5b depict visual explanations of space charge orientation and polarization, within dielectrics of a CMUT cell, respectively.
Figure 5B:
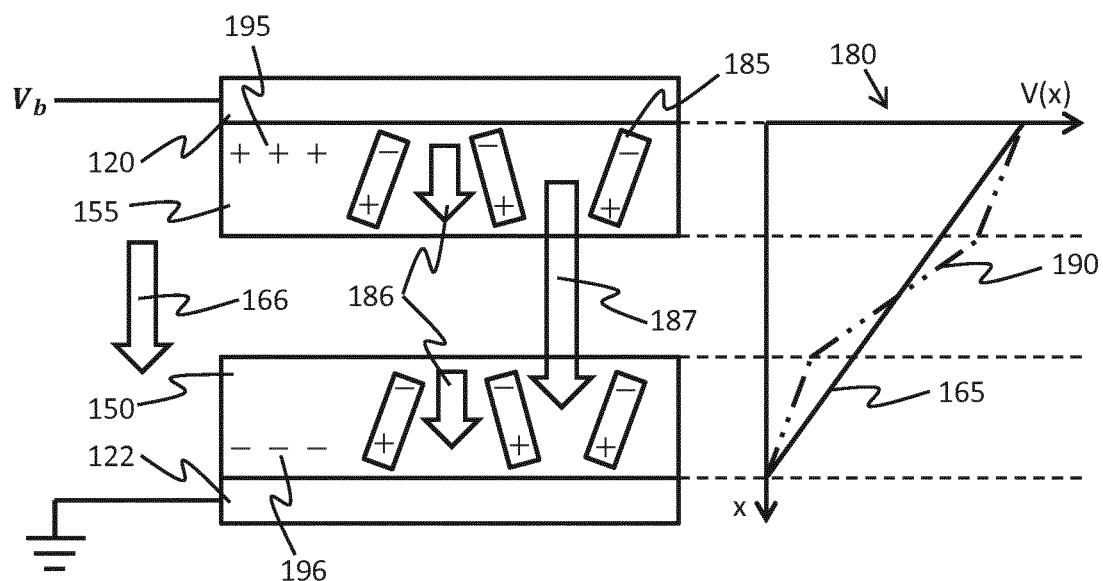

FIGS. 5a and 5b show the effects of space charge orientation and polarization, respectively, on the bias voltage of a CMUT cell.

FIG. 5a depicts a typical CMUT cell with a first electrode 122, a first dielectric 150, a second electrode 120 and a second dielectric 155. The first electrode 122 is electrically grounded and a positive bias voltage, $V_b$, is applied to the second electrode 120. A graph 160 of voltage against position within the CMUT cell depicts a first voltage profile 165 across the CMUT cell when the bias voltage is first applied. The application of the bias voltage establishes an electric field 166 between the first and second electrodes. The electric field strength typically lies in the range of 3.5 MV/cm to 6 MV/cm.

Charge carriers, such as electrons and holes, within the conduction bands of the first and second dielectrics move in response to the electric field. In this example, the second electrode is positive, meaning that the electrons in the first 150 and second 155 dielectric will gravitate towards the second electrode 120. In a similar manner, the positive charge of the second electrode 120 will repel positive charge carriers in the first and second dielectric, resulting in a collection of positive charges near the first electrode 122. The distribution of these charges across the dielectrics is referred to as space charge. In this case, the orientation of the space charge produces an electric field that acts to oppose the electric field 166 generated by the first and second electrodes. This leads to a positive shift in the voltage profile across the cell, which in turn leads to a reduced electric field 171, having a reduced electric field strength compared to electric field 166. As the electric field strength between the electrodes is proportional to the voltage and distance between the electrodes, the gradients of the voltage profiles 165 and 170 can be used as an indication of the change in electric field strength.

In this manner, the orientation of the space charges within the CMUT cell leads to a positive shift in the collapse voltage Vc (i.e. a positive drift). Since the electrical field in the gap is reduced, a larger voltage is needed to bring the membrane into collapse. In other words, at constant bias voltage the membrane would drift out of collapse.

FIG. 5b depicts the dielectric polarization that occurs in the same CMUT cell as depicted in FIG. 5a under the same bias voltage, $V_b$. The graph 180 depicts the voltage profile 165 across the cell generated by the application of the bias voltage. Once again, the bias voltage results in the generation of an electric field 166.

The molecules that make up the dielectric layer behave as electric dipoles 185, each with an associated dipole moment. In the absence of an external electric field, the electric dipole moments of all of the molecules will be randomly aligned. When an external electric field 166 is applied to the dielectrics, the electrical dipole moments of the molecules will align with the electric field, as shown in FIG. 5b. This leads to a reduced electric field 186 within the dielectric layers and an enlarged electric field 187 between the electrodes. This is represented as a voltage profile 190 on the graph 180. The polarization of the dielectric layers due to the electric field leads to a negative shift of the collapse voltage Vc across the cell. As the electrical field is increased in the gap by polarization of the dielectrics, a lower voltage is needed to bring the membrane into collapse. In other words: at contact bias voltage, the membrane would go deeper into collapse due to the increased field in the gap.

This negative voltage drift is further reinforced by the injection of charge carriers 195 and 196 into the dielectric layers from the electrodes by tunneling.

Figure 6:
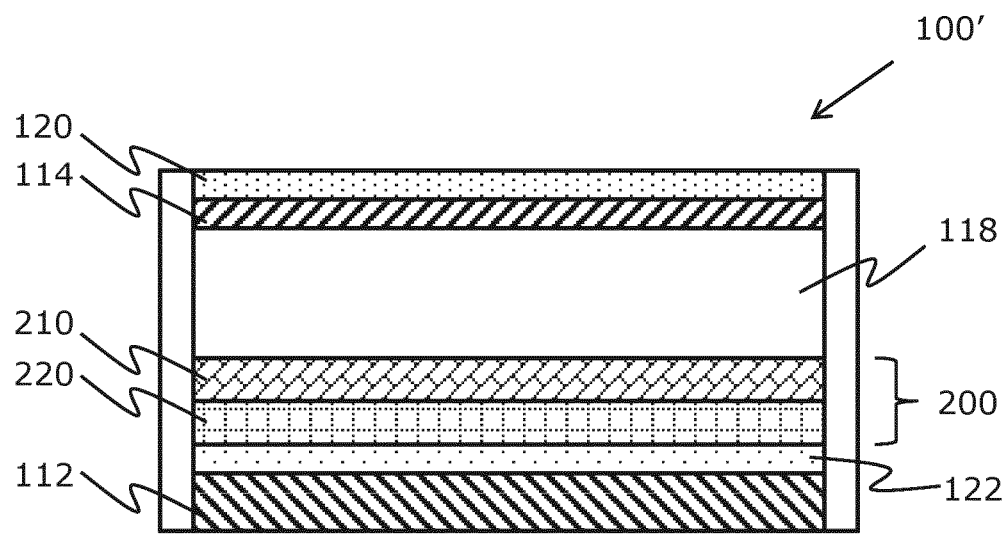
FIG. 6 depicts an embodiment of an RFMEMS.

FIG. 6 shows a capacitive radio frequency micro-electromechanical switch 100', RFMEMS, according to an aspect of the invention. It may comprise a CMUT cell or another type of capacitive MEMS, such as capacitive switches used in pressure sensors and microphones. To illustrate the similarities with the CMUT cell described above, the same reference numbers are used for corresponding components.

The switch includes a substrate 112 and a first electrode 122 connected to said substrate. The first electrode may be connected to the top surface of the substrate as depicted in FIG. 6; however, it may also be positioned within the substrate or form a layer of the substrate itself. In addition, there is provided a dielectric stack 200 connected to the first electrode, such that the dielectric stack separates the first electrode and the substrate from the gap 118. The gap may be filled with a gas or it may be a partial vacuum.

The switch further comprises a flexible membrane 114 and a second electrode 120 connected to said membrane. The flexible membrane and second electrode are spatially separated from the dielectric stack, first electrode and substrate by the gap 118. FIG. 6 depicts the second electrode as being connected to the top surface of the flexible membrane; however, it may be provided within the membrane, form a layer of the membrane or be connected to the bottom surface of the membrane.

The dielectric stack comprises a first dielectric layer 210 and a second dielectric layer 220. FIG. 6 depicts the first dielectric layer as being connected to the top surface of the second dielectric layer; however, the dielectric layer may also be reversed so that the second dielectric layer is connected to the top surface of the first dielectric layer.

The first dielectric layer 210 is adapted to contain a first density of electrically active defects. The electrically active defects, also known as traps, contribute to the strength of polarization effects that occur within a dielectric material under the influence of an electric field. The first dielectric layer is adapted to contain a density of electrically active defects that result in the polarization effects dominating over the orientation of space charges. In this way, it is possible for the first dielectric layer to result in a negative shift in the collapse voltage of the capacitive RFMEMS.

In other words, the first dielectric layer 210 produces a negative drift voltage.

The second dielectric layer 220 is adapted to contain a second density of electrically active defects, lower than the first density within the first dielectric layer. The electrically active defect density of the second layer can lead to the orientation of space charges dominate over the polarization effects under the influence of an electric field. In this way, the second dielectric layer produces a positive shift in the collapse voltage of the capacitive RFMEMS.

In other words, the second dielectric layer 220 produces a positive drift voltage.

Through the combination of the first dielectric layer 210 and the second dielectric layer 220 in a dielectric stack 200, the negative drift voltage and the positive drift voltage act to cancel each other out. In this way, the overall drift voltage produced by dielectric charging in the switch may be reduced, improving both its lifetime and function. The first and second dielectric layers may be constructed from the same material.

A commonly used dielectric material is silicon dioxide, SiO2, which may be prepared in different ways in order to produce different dielectric properties. The first dielectric layer may be constructed using atomic layer deposition, ALD, and the second dielectric layer may be constructed using chemical vapor deposition, CVD.

Atomic layer deposition is a thin film deposition method, wherein a film of a given material is grown on a surface by exposing it to alternate gaseous species. In the case of SiO2, atomic layer deposition leads to a greater number of electrically active defects in the bulk of the material, leading to a greater susceptibility to polarization effects under an electric field. In this way, the first dielectric layer 210 will exhibit a negative drift voltage.

In a similar manner to ALD, CVD is the deposition of a desired material on a surface when the surface is exposed to a volatile precursor gas. In the case of SiO2, a precursor gas of tetraethylorthoscilicate, TEOS, can be used. Dielectric layers produced in this manner are less susceptible to polarization effects than those produced by ALD, due to a reduced number of electrically active defects. This allows the orientation of space charges to dominate the dielectric charging effects due to the electric field. In this way, the second dielectric layer 220 will exhibit a positive drift voltage.

In this arrangement, polarization effects of the first dielectric layer 210, manufactured from SiO2 using ALD, will produce a larger negative drift voltage compared to the positive drift voltage produced by the second dielectric layer 220, manufactured from SiO2 using CVD. In order to minimize the overall drift voltage of the capacitive RFMEMS 100, the second dielectric layer can be made thicker, in order to match the magnitude of the voltage drift of the first layer. In this case, the second dielectric layer is for example at least two times thicker, for example three times thicker, than the first layer. In addition to the relative thickness between the dielectric layers, the absolute thickness of the dielectric stack may be optimized in order to reduce the drift voltage.

In cases where different materials, such as aluminum dioxide, Al3O2, or hafnium(IV) oxide, and/or manufacturing methods are used, the ratio of the thicknesses of the first and second layer may be altered in order to further optimize the minimization of the drift voltage.

Figure 7:
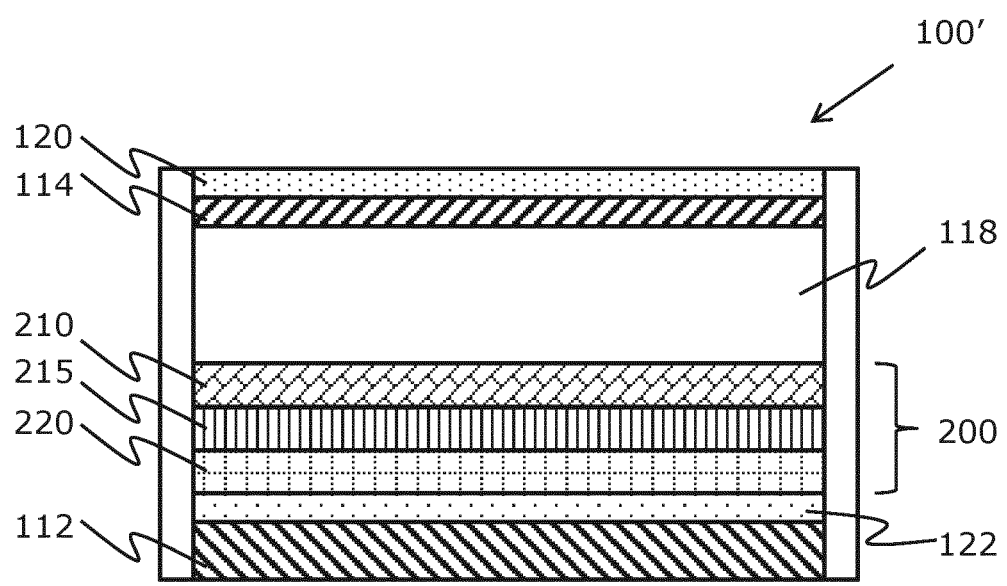
FIG. 7 depicts another embodiment of an RFMEMS.

FIG. 7 shows another embodiment of a capacitive RFMEMS 100' according to an aspect of the invention. As shown in the figure, the dielectric stack 200 can further comprise a third dielectric layer 215. The other layers are as described with referenced to FIG. 6. This layer 215 may be selected based on the dielectric properties of the first 210 and second 220 dielectric layers. The dielectric properties of a material may be ascertained through trap spectroscopy by charge injection and sensing, TSCIS, or leakage current spectroscopy (LCS). TCIS is sensitive to the interface states of a material, wherein a lower number of interface states may serve as an indication that the material will produce a positive drift voltage. LCS is sensitive to the bulk states of a material. A higher number of bulk states in a material leads to larger polarization effects under the influence of an electric field.

The inclusion of the third dielectric layer may allow the minimization of the drift voltage to be further optimized. In the case where the first and second dielectric layers are both made from SiO2, the third dielectric layer may be constructed from aluminum oxide, AL2O3.

The capacitive RFMEMS shown in FIGS. 6 and 7 may be a capacitive micro-machined ultrasound transducer, CMUT, cell for use in an ultrasound imaging system. A detailed description of a typical ultrasound imaging system is described further below in relation to FIG. 13.

A basic ultrasound system may include an ultrasonic probe, comprising an array of CMUT cells as described with reference to FIGS. 6 and 7, and a voltage supply adapted to provide a bias voltage to the first electrode 122 and a stimulus voltage to the second electrode 120. In other cases, the bias voltage may be provided to the second electrode and the stimulus voltage provided to the first electrode.

The bias voltage may drive the CMUT cell into collapse mode, wherein the flexible membrane 114 contacts the dielectric stack 200, reducing the size of the gap 118. This increases the electric field density in the collapsed portion of the CMUT, leading to detrimental charging effects. By providing CMUT cell with a dielectric stack adapted to cancel out the detrimental charging effects, the lifetime and performance of the ultrasonic probe may be increased.

The stimulus voltage may cause the flexible membrane of the CMUT cell to vibrate at a predetermined frequency. In this way, the CMUT cell is able to generate an ultrasonic pulse. This feature also applies in reverse, meaning that the flexible membrane may vibrate in response to incoming vibrations. The vibrations cause a change in capacitance of the CMUT cell which may be detected by the second electrode 120 in the form of electrical signals. These electrical signals may then be interpreted by a signal processor and used to generate image data for constructing an ultrasound image.

Figure 8:
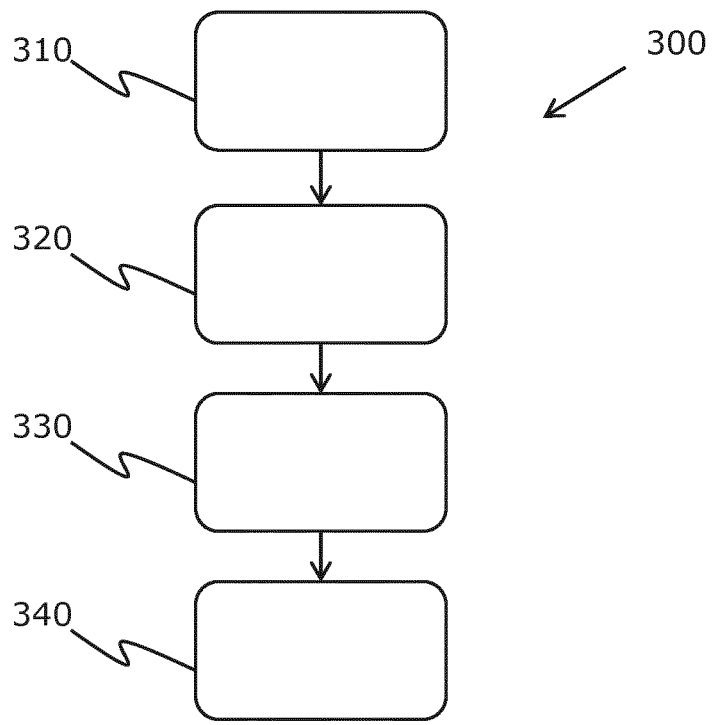
FIG. 8 schematically depicts a method of operating the RFMEMS of FIGS. 5 and 6.

FIG. 8 depicts a method 300 of operating a capacitive RFMEMS as described with reference to FIGS. 6 and 7.

In step 310, a bias voltage is provided to the first electrode 120 of a capacitive RFMEMS. This bias voltage may be above a predetermined value, known as the collapse voltage, which drives the CMUT cell into a collapse mode. This bias voltage establishes an electric field between the first and second electrodes.

In step 320, a stimulus voltage is provided to the second electrode in order to produce an ultrasonic RF pulse by causing the non-collapsed portions of the flexible membrane to vibrate. This stimulus voltage increases the electric field density within the switch, particularly in the collapsed portion.

In step 330, the increased electric field causes the first dielectric layer to become polarized to a first degree of polarization and the second dielectric layer to become polarized to a second degree, lower than the first degree. This generates a negative drift voltage.

In step 340, the first dielectric layer undergoes space charge orientation to a first level and the second dielectric layer undergoes space charge orientation to a second level, greater than the first level. The orientations of the space charges across the two dielectric layers, by the electric field, generate a positive drift voltage. In this way the overall drift voltage of the switch is reduced.

The dielectric stack arrangement has been described above in connection with a circular substrate electrode and a ring shaped membrane electrode. However, this is only an example. The dielectric stack design may be used with solid (i.e. not annular) electrodes as in the example of FIG. 1.

Figure 9A:
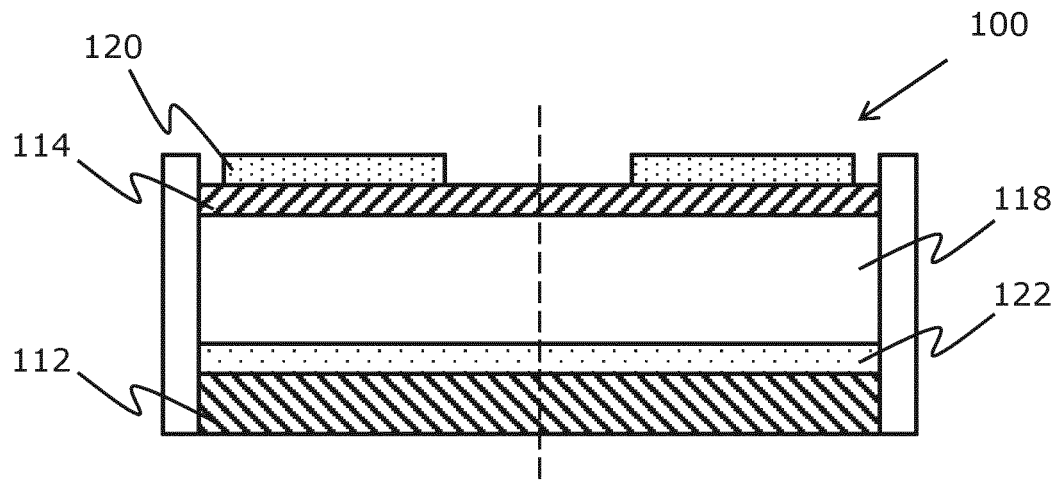
FIGS. 9a and 9b depict a CMUT cell, according to an embodiment, in relaxed and collapsed mode respectively.
Figure 9B:
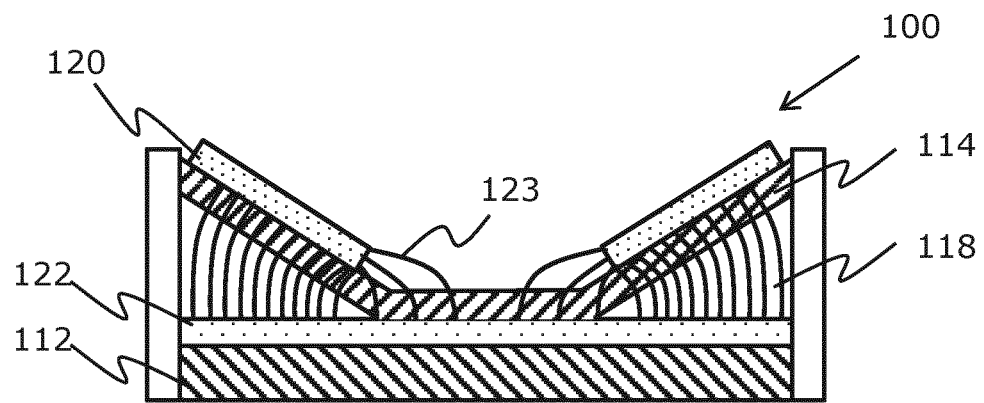

FIGS. 9a and 9b depict an embodiment of a CMUT cell 100, in relaxed and collapse mode respectively. Again, layers which perform the same functions as in previous examples are given the same reference numbers. The CMUT cell 100 includes a substrate 112 and a first electrode 122 connected to said substrate. The CMUT cell additionally includes a flexible membrane 114 and a second electrode 120, which are spatially separated from the first electrode and substrate by a gap 118. The second electrode is formed in the shape of a ring. The ring shape of the second electrode 120 is not limited to being purely circular, but may take any shape where a central portion of the shape has been removed.

In other words, the second electrode 120 is shaped so that the electrode does not occupy a middle portion of the flexible membrane. More specifically, the second electrode is shaped so that the portion of the flexible membrane contacting the first electrode, when in collapse mode as shown in FIG. 9b, is not connected to the second electrode. FIG. 9b depicts electric field lines 123 that describe the electric field generated when the first electrode is grounded and the bias voltage is applied to the second electrode. The electric field density is highest between the electrodes, shown by the small spacing between the electric field lines. By removing the central portion of the second electrode, the electric field density is reduced in the collapsed portion of the CMUT cell, as shown by the large spacing between the electric field lines, thereby reducing the level of charging effects, such as dielectric polarization, charge injection and space charge orientation. This results in a longer lifetime and improved performance of the CMUT cell.

The design of FIG. 9a does not have any dielectric stack. However a single layer dielectric, or the two or three layer dielectric stack described above may additionally be used as described further below with reference to FIG. 12. There may for example be a single or multiple layer dielectric on the bottom electrode 122 and also a single or multiple layer dielectric below the top electrode 120.

Figure 10A:
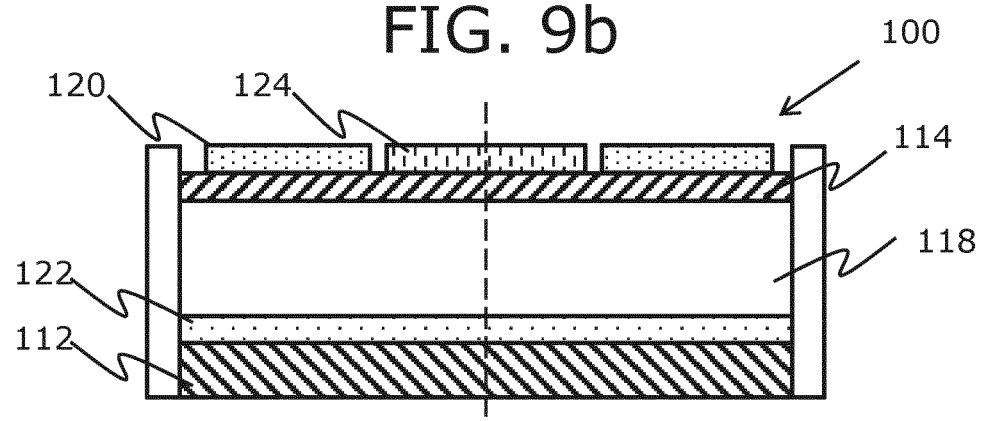
FIGS. 10a and 10b depict a CMUT cell, according to another embodiment, in relaxed and collapsed mode respectively.
Figure 10B:
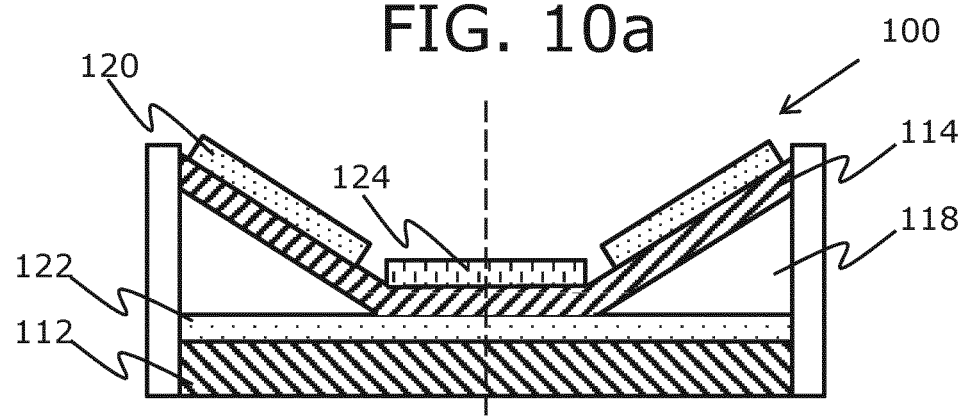

FIGS. 10a and 10b depict an embodiment of a CMUT cell, in relaxed and collapse mode respectively, according to a further aspect of the invention. The same layers as used in FIGS. 9a and 9b are given the same reference numbers and the description is not repeated. In this case, the CMUT cell includes a third electrode 124 occupying the middle portion of the second electrode. The third electrode may enable a greater level of control of the electric field density in the collapsed portion of the CMUT cell.

For example, the third electrode may be electrically grounded. In this way, the electric field due to the stimulus voltage is removed, meaning that only the electric field due to the bias voltage remains in the collapsed portion of the CMUT cell. This further reduces the electric field density in this portion of the cell, thereby further reducing the charging effects within the cell.

The ring electrode and central (third) electrode may instead be formed on the substrate as the lower first electrode 122 and the upper membrane electrode 120 may then be a continuous electrode.

Thus, one of the first and second electrodes comprises a ring, and there is a third electrode which occupies a middle portion of the ring such that the ring and third electrodes are spatially separated.

Figure 11:
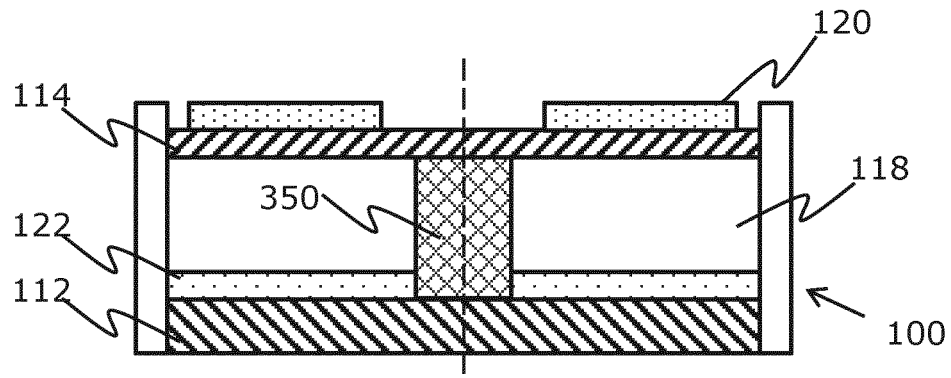
FIG. 11 depicts a pre-stressed CMUT cell according to an embodiment.

FIG. 11 depicts another embodiment of a CMUT cell 100 according to a further aspect of the invention. This embodiment shows a CMUT cell similar to the one depicted in FIGS. 9a and 9b with an additional support 350 connected between the flexible membrane 114 and the substrate. In order to accommodate the support, the first electrode 122 is made into the shape of a ring, wherein the support occupies the middle portion of the ring. Thus, in this design both the first and second electrodes each comprise a ring, and the support 350 is formed about the central axis, connected between the substrate and the flexible membrane.

The support 350 enables the CMUT cell to operate in a pre-stressed mode, which provides many of the benefits of operating the CMUT cell in collapsed mode with a reduced electric field density between the electrodes. In this way, the charging effects of the CMUT cell are reduced.

Figure 12A:
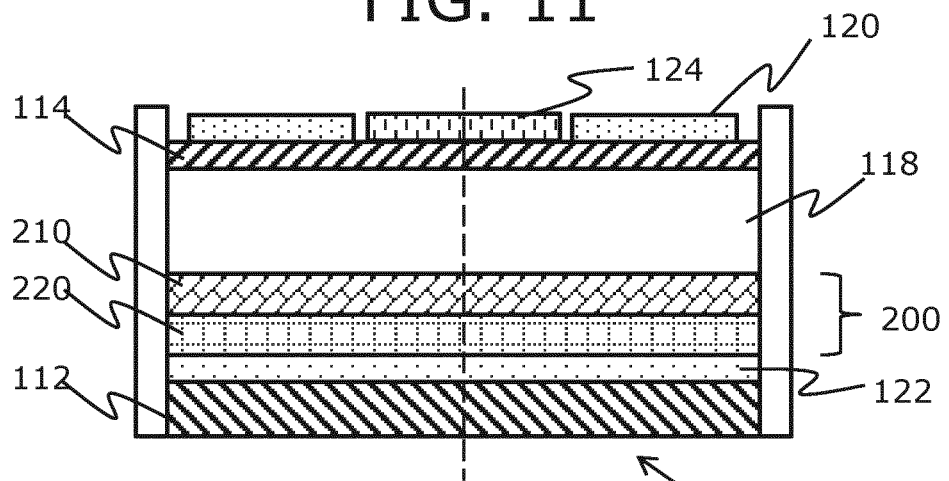
FIGS. 12a and 12b depict a CMUT cell, according to yet another embodiment, in relaxed and collapsed mode respectively.
Figure 12B:
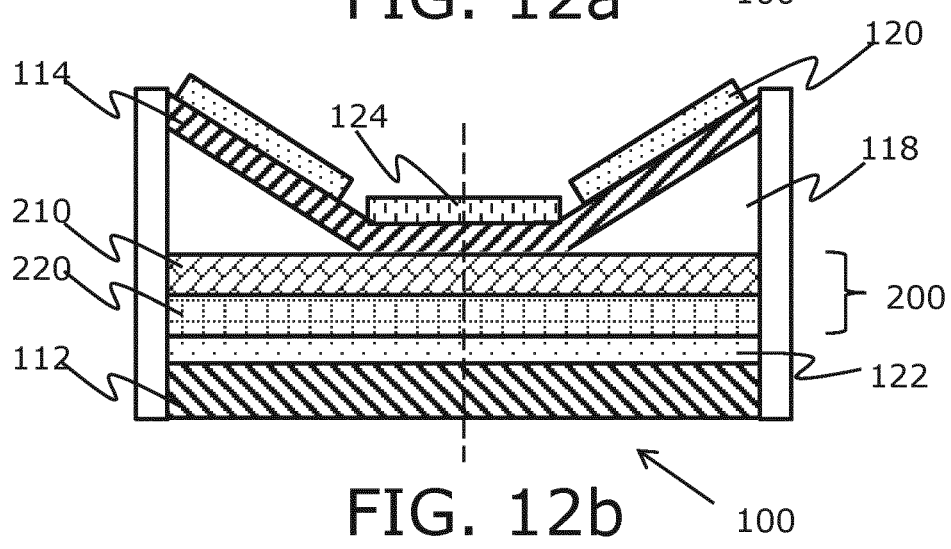

FIGS. 12a and 12b depict yet another embodiment of a CMUT cell, in relaxed and collapse mode, according to the further aspect of the invention. According to this arrangement, a CMUT cell is provided with a second electrode 120 in the shape of a ring and an electrically grounded third electrode 124, as shown in FIGS. 10a and 10b, and a dielectric stack 200 containing a first dielectric layer 210 and a second dielectric layer 220, as shown in FIG. 6.

In this design, an electrode configuration adapted to minimize the charging effects of the electric field, when the CMUT cell is operated in collapse mode, is combined with a dielectric stack adapted to cancel out any remaining charging effects. In this way it is possible to minimize, or eliminate, any charging effects, and therefore voltage drift, in the CMUT cell, thereby further improving both the lifetime and performance of the cell further.

Figure 13:
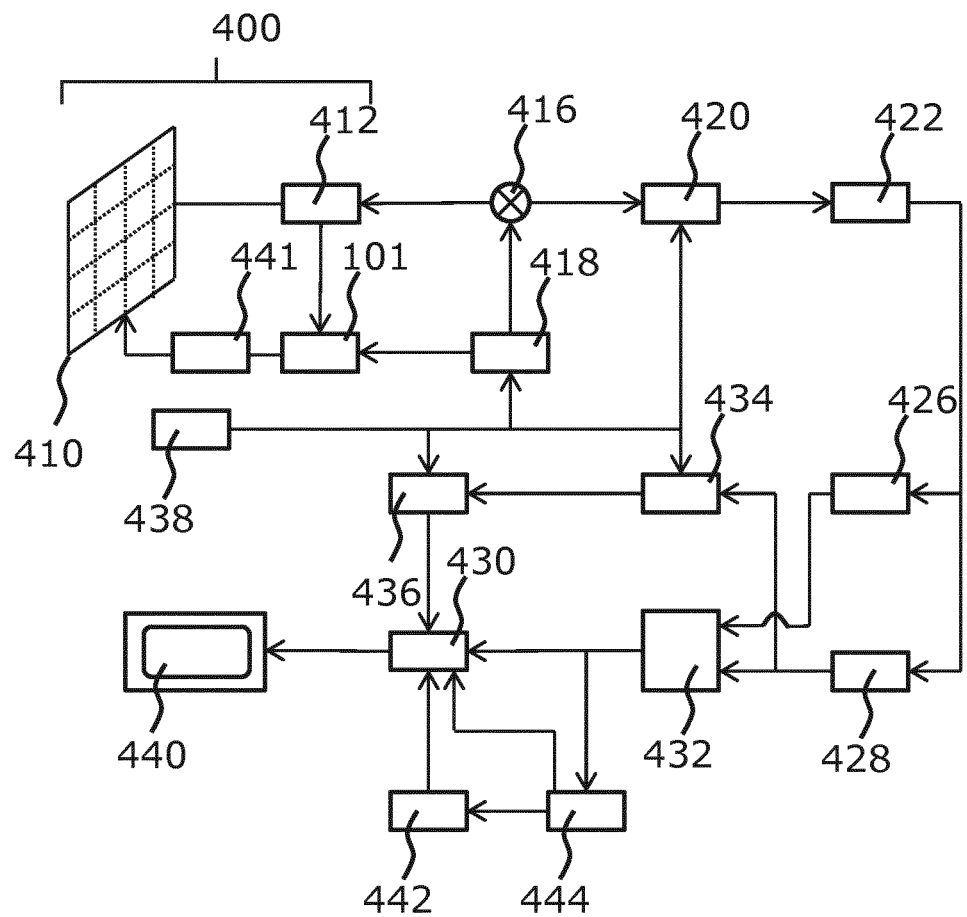
FIG. 13 schematically depicts an example embodiment of an ultrasound diagnostic imaging system.

In FIG. 13, an ultrasonic diagnostic imaging system with an array transducer probe 400 according to an example embodiment of the present invention is shown in block diagram form. In FIG. 13 a CMUT transducer array 410, comprising CMUT cells as discussed above, is provided in an ultrasound probe 400 for transmitting ultrasonic waves and receiving echo information. The transducer array 410 may be a one- or a two-dimensional array of transducer elements capable of scanning in a 2D plane or in three dimensions for 3D imaging.

The transducer array 410 is coupled to a microbeam former 412 in the probe 410 which controls transmission and reception of signals by the CMUT array cells. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 412 is coupled by the probe cable, e.g. coaxial wire, to a transmit/receive (T/R) switch 416 which switches between transmission and reception modes and protects the main beam former 420 from high energy transmit signals when a microbeam former is not present or used and the transducer array 410 is operated directly by the main system beam former 420. The transmission of ultrasonic beams from the transducer array 410 under control of the microbeam former 412 is directed by a transducer controller 418 coupled to the microbeam former by the T/R switch 416 and the main system beam former 420, which receives input from the user's operation of the user interface or control panel 438. One of the functions controlled by the transducer controller 418 is the direction in which beams are steered and focused. Beams may be steered straight ahead from (orthogonal to) the transducer array 410, or at different angles for a wider field of view. The transducer controller 418 may be coupled to control the aforementioned voltage source 101 for the CMUT array. For instance, the voltage source 101 sets the DC and AC bias voltage(s) that are applied to the CMUT cells of a CMUT array 410, e.g. to generate the ultrasonic RF pulses in transmission mode as explained above.

The partially beam-formed signals produced by the microbeam former 412 are forwarded to the main beam former 420 where partially beam-formed signals from individual patches of transducer elements are combined into a fully beam-formed signal. For example, the main beam former 420 may have 128 channels, each of which receives a partially beam-formed signal from a patch of dozens or hundreds of CMUT transducer cells 100. In this way the signals received by thousands of transducer elements of a transducer array 410 can contribute efficiently to a single beam-formed signal.

The beam-formed signals are coupled to a signal processor 422. The signal processor 422 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 422 optionally may perform additional signal enhancement such as speckle reduction, signal compounding, and noise elimination. The bandpass filter in the signal processor 422 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 426 and optionally to a Doppler processor 428. The B-mode processor 426 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 428, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. The structural and motion signals produced by the B-mode (and Doppler) processor(s) are coupled to a scan converter 432 and a multiplanar reformatter 444. The scan converter 432 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 444 will convert echoes which are received from points in a common plane in a volumetric region of the body into an ultrasonic image of that plane, for instance as described in U.S. Pat. No. 6,443,896 (Detmer). A volume renderer 442 converts the echo signals of a 3D data set into a projected 3D image as viewed from a given reference point as described in U.S. Pat. No. 6,530,885 (Entrekin et al.)

The 2D or 3D images are coupled from the scan converter 432, multiplanar reformatter 444, and volume renderer 442 to an image processor 430 for further enhancement, buffering and temporary storage for display on an image display 440. In addition to being used for imaging, the blood flow values produced by the Doppler processor 428 and tissue structure information produced by the B-mode processor 426 are coupled to a quantification processor 434. The quantification processor produces measures of different flow conditions such as the volume rate of blood flow as well as structural measurements such as the sizes of organs and gestational age. The quantification processor may receive input from the user control panel 438, such as the point in the anatomy of an image where a measurement is to be made.

Output data from the quantification processor is coupled to a graphics processor 436 for the reproduction of measurement graphics and values with the image on the display 440. The graphics processor 436 can also generate graphic overlays for display with the ultrasound images. These graphic overlays can contain standard identifying information such as patient name, date and time of the image, imaging parameters, and the like. For these purposes the graphics processor receives input from the user interface 438, such as patient name.

The user interface is also coupled to the transmit controller 418 to control the generation of ultrasound signals from the transducer array 410 and hence the images produced by the transducer array and the ultrasound system. The user interface is also coupled to the multiplanar reformatter 444 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 412 and/or the Doppler processor 428 may be omitted, the ultrasound probe 410 may not have 3D imaging capabilities and so on. Other variations will be apparent to the skilled person.

Moreover, it will be understood that the present invention is not limited to an ultrasonic diagnostic imaging system. The teachings of the present invention are equally applicable to ultrasonic therapeutic systems in which the CMUT cells 100 of the probe 400 may be operable in transmission mode only as there is no need to receive pulse echoes. As will be immediately apparent to the skilled person, in such therapeutic systems the system components described with the aid of FIG. 12 and required to receive, process and display pulse echoes may be omitted without departing from the teachings of the present application.

Figure 14:
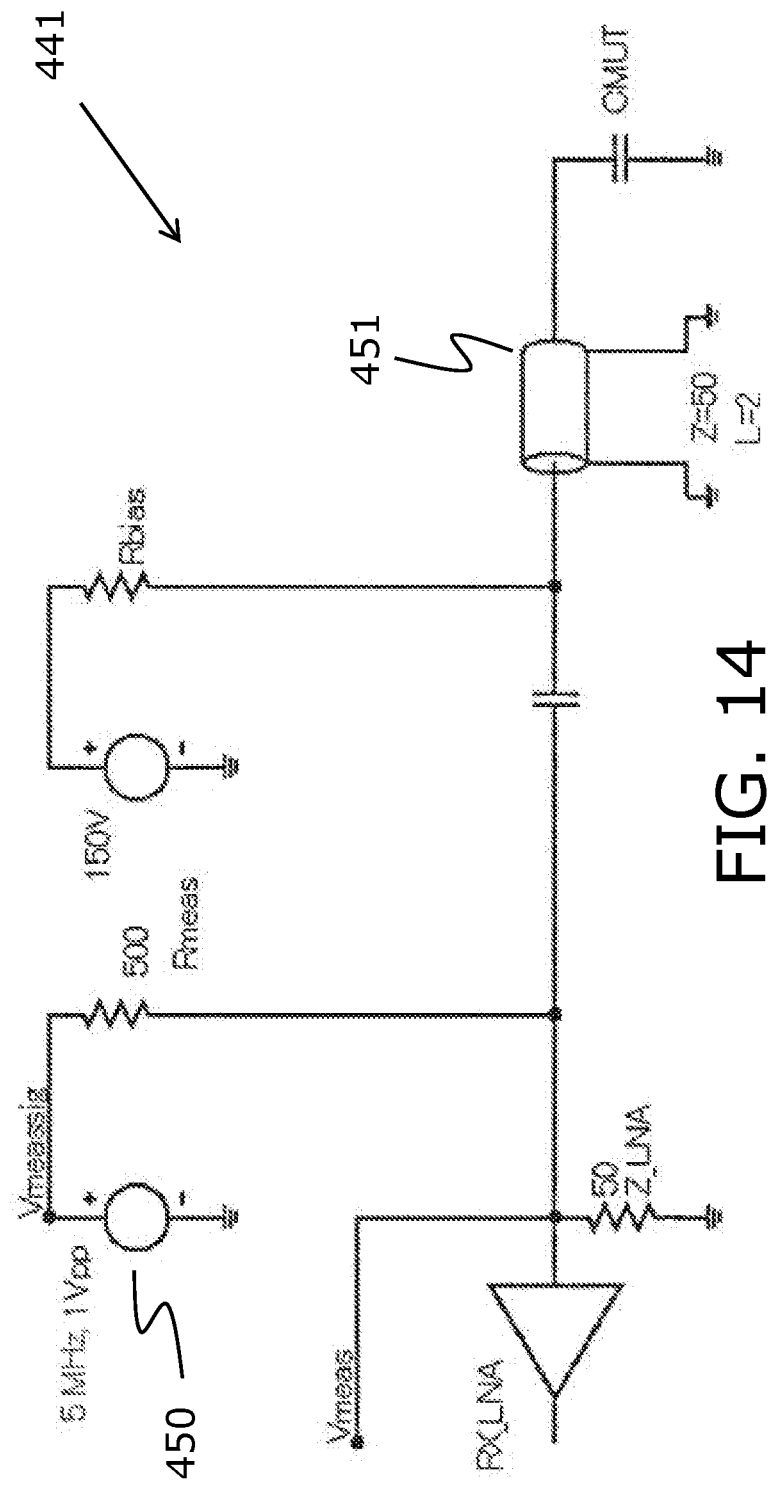
FIG. 14 depicts an example of a capacitance sensing circuit.

According to the further aspect of the invention, the ultrasound system further comprises a capacitance sensing circuit 441. FIG. 14 shows an embodiment of the capacitance sensing circuit. The capacitance sensing circuit may be adapted to produce a test signal with a known voltage. For example, a generator 450 can be used to generate a small, sinusoidal test signal, of a known voltage, $V_{meassig}$, that propagates through the ultrasound system. The test signal is injected into the ultrasound system by way of a large resistor, $R_{meas}$. The resistance of $R_{meas}$ may be for example 500Ω.

As the signal travels through the capacitance sensing circuit, it will undergo attenuation due to the impedance of the various components of the ultrasound system, such as a low noise amplifier (RX_LNA), a coaxial cable 451, and a CMUT cell (CMUT). The impedance of a component is proportional to the component's capacitance. The drift voltage of a CMUT cell, caused by the charging effects discussed above, leads to a change in the capacitance of the cell. By monitoring the capacitance of the CMUT cell, it is possible to monitor the level of charging induced by the electric field within the cell. The impedance of a CMUT cell is given by the following formula:

$$|Z_{CMUT}| = \frac{1}{2\pi f \times C_{CMUT}}$$

wherein: $|Z_{CMUT}|$ is the magnitude of the impedance of the CMUT cell; f is the frequency of the test signal, which is selected from a range of signals appropriate for the operation of the CMUT cell and the capacitance sensing circuit; and $C_{CMUT}$ is the capacitance of the CMUT cell.

In an example where the test signal of the capacitance sensing circuit is attenuated by a low-noise amplifier (RX_LNA), a coaxial cable 451 and the CMUT cell, the attenuated signal can be described using the following formula:

$$V_{meas} = \frac{Z_{lna}/Z_{in}}{R_{meas} + Z_{lna}/Z_{in}} V_{meassig}$$

wherein: $V_{meas}$ is the voltage (amplitude) of the attenuated signal; $Z_{lna}$ is the impedance of the low-noise amplifier; $Z_{in}$ is the combined impedance of the coaxial cable and CMUT cell; $R_{meas}$ is the resistance of the resistor used to inject the test signal into the ultrasound system; and $V_{meassig}$ is the voltage (amplitude) of the test signal.

As the impedance of the coaxial cable is known from its length and characteristics, the impedance of the CMUT cell can be extracted from the value of $Z_{in}$. In the example shown in FIG. 14, the length of the coaxial cable is two meters, leading to an impedance of 50Ω. As shown above, the value of the impedance of the CMUT cell can be used to calculate the cell's capacitance. This then leads to a drift voltage of the CMUT cell, which indicates the level of charging occurring within the cell.

If the capacitance sensing circuit determined that the absolute voltage drift is above a predetermined value, selected to be a value where the charging effects become detrimental to the function of the ultrasound system such as 10V or 5V, the voltage supply 45 may be adapted to reverse the polarity of the bias voltage, the stimulus voltage, or both. By reversing the polarity of the voltages supplied to the CMUT cell, the electric field generated between the electrodes is reversed. In this way, the dielectric polarization and space charge orientations may be reduced, or eliminated. By performing the polarity reversal in less than 1 microsecond, acoustic artifacts are avoided in the final image of the ultrasound image produced by the system.

Figure 15:
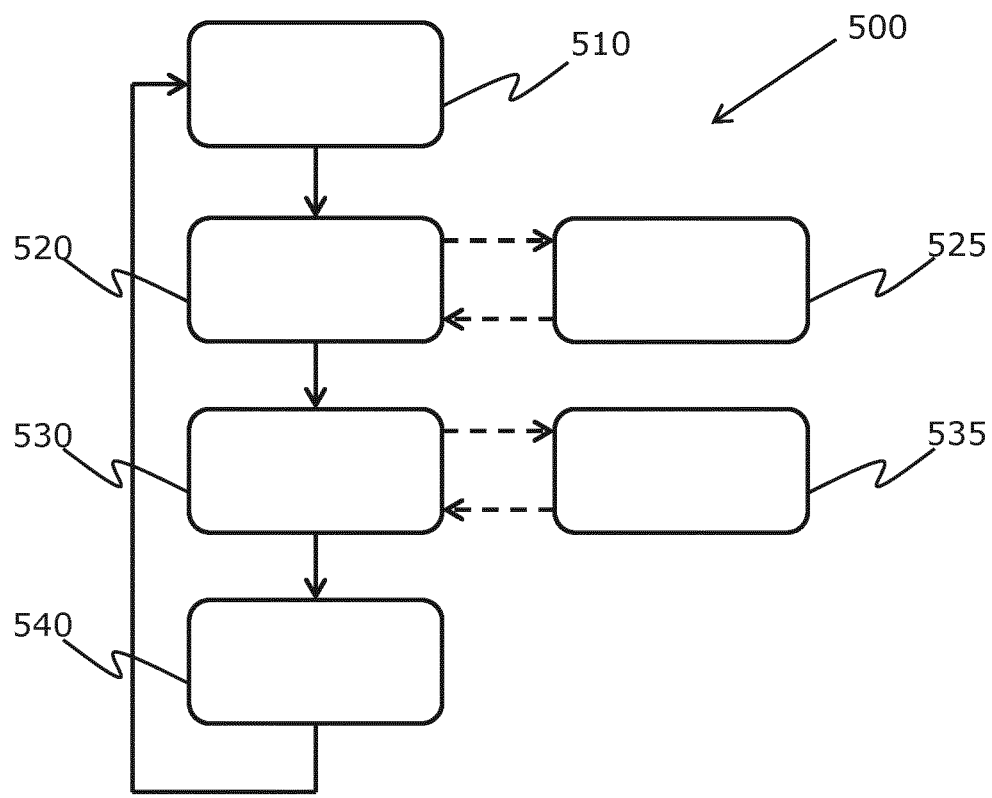
FIG. 15 depicts a method of operating a CMUT cell.

FIG. 15 depicts a method 500 of operating a CMUT cell. In step 510, a drift voltage is determined for the CMUT cell. A method for performing this step is described with reference to FIG. 16.

In step 520, a bias voltage is provided to the first electrode of the CMUT cell, wherein the bias voltage is selected based on the determined voltage drift. The magnitude of the bias voltage is above the threshold for driving the CMUT cell into collapse mode.

By selecting the bias voltage based on the determined voltage drift, the charging effects experienced by the CMUT cell can be reduced or eliminated. For example, based on the determined voltage drift, the method may progress to step 525, wherein the polarity of the bias voltage is reversed from the previous cycle in order to reverse the electric field direction between the electrodes of the cell. This may be done if it is determined, in step 510, that the magnitude of the voltage drift is above a predetermined value. This step is described in more detail further below with reference to FIGS. 17 and 18.

In step 530, a stimulus voltage may be provided to the second electrode of the CMUT cell in order to cause the flexible membrane to vibrate at a predetermined frequency. In this way, an ultrasonic RF pulse may be generated by the CMUT cell.

In a similar manner to above, if it is determined that the voltage drift is above a predetermined value, the polarity of the stimulus voltage may be reversed in step 535. In this way, charging effects may be further reduced or eliminated. This step is described in more detail further below with reference to FIGS. 17 and 18.

In step 540, the stimulus voltage is removed in order to enable the flexible membrane to vibrate freely in response to incoming signals. These signals may be the reflected ultrasonic waves generated in step 530. Following the reception period, the method returns to step 510 in order to operate in a cyclical manner.

Figure 16:
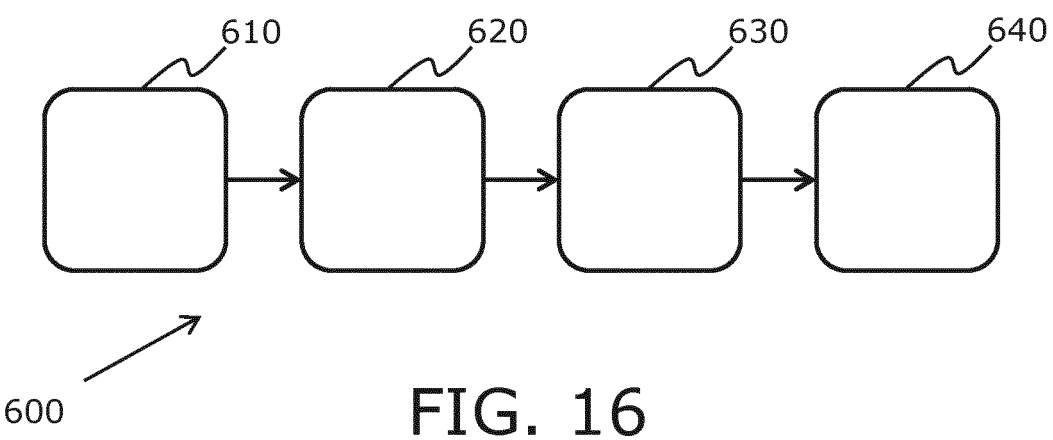
FIG. 16 depicts an embodiment of the method of FIG. 15.

FIG. 16 depicts a method 600 for determining a voltage drift of a CMUT cell. In step 610, a test signal is generated at a predetermined voltage. This test signal may then be injected into the ultrasound system.

In step 620, an attenuated signal is measured of the test signal. The attenuated signal is attenuated by at least the impedance of the CMUT cell before it is measured.

In step 630, the impedance of the CMUT cell is determined based on the test signal and the attenuated signal.

In step 640, a voltage drift of the CMUT cell is determined based on the determined impedance of the CMUT cell.

These steps are described in detail above with reference to the capacitance sensing circuit 441 in FIGS. 13 and 14.

Figure 17:
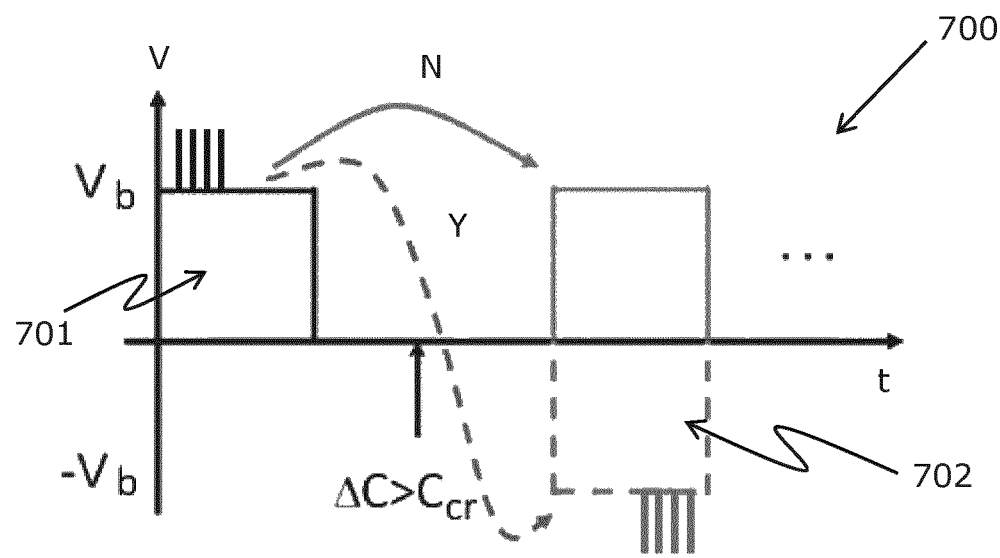
FIG. 17 depicts another embodiment of the method of FIG. 15.

FIG. 17 depicts a method 700 for reversing the polarity of the bias voltage (Vb) and stimulus voltage (RF driving). During the first imaging sequence 701, a bias voltage and stimulus voltage are applied to the CMUT cell in order to transmit an ultrasonic RF pulse. The CMUT cell is then held in receive mode by the bias voltage as the stimulus voltage is removed. Following the imaging sequence, the drift voltage of the CMUT cell is determined as described above with reference to FIG. 16. As the drift voltage is dependent on the capacitance of the CMUT cell, a drift capacitance ($\Delta C$) may be determined. If $\Delta C$ is greater than a critical value ($C_{cr}$) then the polarity of the bias voltage, and the stimulus voltage, may be reversed for the second imaging sequence 702 in order to reduce the drift voltage of the CMUT cell. If $\Delta C$ is less than $C_{cr}$, then the polarity may remain the same as in the first imaging sequence as the drift voltage is not yet high enough to result in detrimental effects to the image quality of the ultrasound system. Thus, there is a determination of whether the drift exceeds the threshold (Y=yes in FIG. 17 and N=no).

Figure 18:
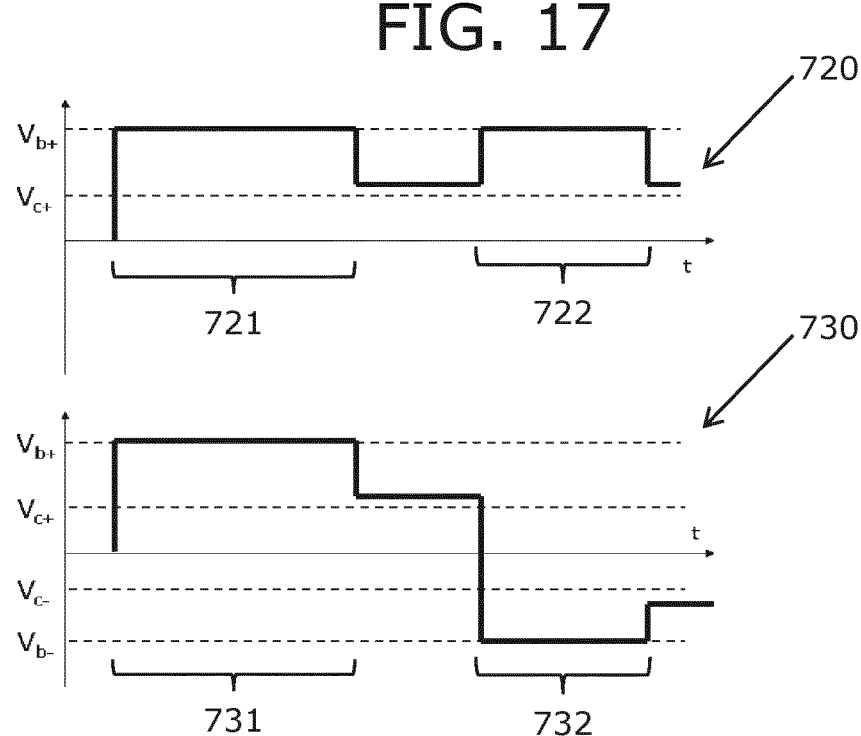
FIG. 18 depicts two embodiments of a bias voltage profile.

FIG. 18 depicts two embodiments of a bias voltage profile that may be applied to the first electrode of a CMUT cell in order to drive the cell into collapse mode. The first bias voltage profile 720 illustrates a method of applying a reduced bias voltage when the CMUT cell is not performing an imaging sequence 721, 722. In this way it is possible to reduce the electric field density within the CMUT cell, thereby reducing the charging effects. As the reduced bias voltage is above the collapse voltage ($V_{C+}$), the CMUT cell remains in collapse mode, meaning that it is prepared for the next imaging sequence.

The second bias voltage profile 730 depicts a similar method of reducing the bias voltage between the first 731 and second 732 imaging sequences; however, in this case the polarity of the bias voltage is reversed in the second imaging sequence 732 as described with reference to FIG. 17. In this way, the charging effects may be reduced by both the reduced bias voltage and the reversed polarity.

The switch to an opposite polarity of the bias voltage is performed rapidly for example within 1 microsecond.

The change in polarity may take place at each subsequent transmission event. In this way, there is a symmetrical square wave bias voltage on which is superposed the transmission pulses. Thus, instead of the polarity switching being dependent on a capacitance measurement as in FIG. 17, it may take place at each sequential transmission.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A capacitive radio frequency micro-electromechanical switch (RFMEMS), comprising:
   a substrate;
   a first electrode connected to the substrate;
   a flexible membrane at least partially spatially separated from the first electrode;
   a second electrode connected to the flexible membrane; and
   a dielectric stack disposed between the first electrode and the second electrode and flexible membrane, comprising:
      a first dielectric layer having a first density of electrically active defects; and
      a second dielectric layer having a second density of electrically active defects, lower than the first, wherein the first and second dielectric layers comprise an oxide of the same material.

2. The capacitive RFMEMS as claimed in claim 1, wherein the first and second dielectric layers comprise silicon dioxide ($SiO_2$).

3. The capacitive RFMEMS as claimed in claim 2, wherein the first dielectric layer is constructed using atomic layer deposition.

4. The capacitive RFMEMS as claimed in claim 2, wherein the second dielectric layer is constructed using chemical vapor deposition.

5. The capacitive RFMEMS as claimed in claim 3, wherein the second dielectric layer has a thickness that is twice a thickness of the first dielectric layer.

6. The capacitive RFMEMS as claimed in claim 1, wherein the first and second dielectric layers comprise aluminum dioxide ($Al_3O_2$) or hafnium(IV) oxide ($HFO_2$).

7. The capacitive RFMEMS as claimed in claim 1, wherein the dielectric stack further comprises:
   a third dielectric layer, wherein the third dielectric layer is selected based on the dielectric properties of the first and second dielectric layer.

8. The capacitive RFMEMS as claimed in claim 7, wherein the first and second dielectric comprise silicon dioxide ($SiO_2$) and the third dielectric layer comprises aluminum dioxide ($Al_3O_2$).

9. The capacitive RFMEMS as claimed in claim 1, wherein the capacitive RFMEMS is a capacitive micromachined ultrasound transducer (CMUT) cell.

10. An ultrasound system comprising:
an ultrasonic probe, wherein the ultrasonic probe comprises an array of CMUT cells each as claimed in claim 9;
a voltage supply coupled to the ultrasonic probe, wherein the voltage supply is adapted to:
provide a bias voltage between the first electrode and second electrode of a CMUT cell, wherein the bias voltage is adapted to drive the CMUT cell into a collapse mode; and
provide a stimulus voltage between the first electrode and second electrode of the CMUT cell.

11. The ultrasonic system as claimed in claim 10, wherein the stimulus voltage is adapted to vibrate the flexible membrane of the CMUT cell at a predetermined frequency.

12. The ultrasonic system as claimed in claim 10, wherein the second electrode is adapted to detect incoming vibrations.

13. The ultrasonic system as claimed in claim 12, wherein the system further comprises:
a signal processor adapted to generate data based on the incoming vibrations detected by the second electrode.

14. A method for operating a capacitive radio frequency micro-electromechanical switch (RFMEMS), the capacitive RFMEMS comprising:
a substrate;
a first electrode connected to the substrate;
a flexible membrane at least partially spatially separated from the first electrode;
a second electrode connected to the flexible membrane; and
a dielectric stack disposed between the first electrode and the second electrode and flexible membrane, comprising:
a first dielectric layer having a first level of electrically active defects; and
a second dielectric layer having a second level of electrically active defects, lower than the first,
the method comprising:
providing a bias voltage to the first electrode of the capacitive RFMEMS, thereby creating an electric field between the first and second electrode, wherein the bias voltage is adapted to drive the capacitive RFMEMS into a collapse mode;
providing a stimulus voltage to the second electrode, thereby increasing an electric field between the first and second electrode;
polarizing the first dielectric layer to a first degree of polarization and the second dielectric layer to a second degree of polarization, lower than the first degree, thereby causing a negative drift in the bias voltage between the first and second electrodes; and
orienting space charges within the first dielectric layer to a first level of orientation and within the second dielectric layer to a second level of orientation, greater than the first level, thereby causing a positive drift in the bias voltage between the first and second electrodes, thereby minimizing the overall drift in bias voltage between the first and second electrodes.

15. The method as claimed in claim 14, wherein the first and second dielectric layers comprise a same material.

16. A capacitive radio frequency micro-electromechanical switch (RFMEMS), comprising:
a substrate;
a first electrode connected to the substrate;
a flexible membrane at least partially spatially separated from the first electrode;
a second electrode connected to the flexible membrane, wherein a bias voltage applied to the first electrode of the capacitive RFMEMS an electric field between the first and second electrode is adapted to drive the capacitive RFMEMS into a collapse mode, and a stimulus voltage applied to the second electrode increases an electric field between the first and second electrode; and
a dielectric stack disposed between the first electrode and the second electrode and flexible membrane, comprising: a first dielectric layer; and a second dielectric layer, the first dielectric layer being polarized to a first degree of polarization and the second dielectric layer to a second degree of polarization, lower than the first degree, causing a negative drift in the bias voltage between the first and second electrodes, wherein: space charges are oriented within the first dielectric layer to a first level of orientation and within the second dielectric layer to a second level of orientation, which is greater than the first level, thereby causing a positive drift in the bias voltage between the first and second electrodes; and an overall drift in bias voltage is reduced between the first and second electrodes.

17. The capacitive RFMEMS as claimed in claim 16, wherein the first and second dielectric layers comprise a same material.

18. An ultrasound system comprising:
an ultrasonic probe, wherein the ultrasonic probe comprises an array of CMUT cells each as claimed in claim 9;
a voltage supply coupled to the ultrasonic probe, wherein the voltage supply is adapted to: provide a bias voltage between the first electrode and second electrode of a CMUT cell, wherein the bias voltage is adapted to drive the CMUT cell into a collapse mode; and provide a stimulus voltage between the first electrode and second electrode of the CMUT cell.

19. The ultrasonic system as claimed in claim 18, wherein the stimulus voltage is adapted to vibrate the flexible membrane of the CMUT cell at a predetermined frequency.

20. The ultrasonic system as claimed in claim 18, wherein the second electrode is adapted to detect incoming vibrations.

21. The ultrasonic system as claimed in claim 20, wherein the system further comprises:
a signal processor adapted to generate data based on the incoming vibrations detected by the second electrode.

* * * * *